(12) United States Patent
Kuzushima et al.

(10) Patent No.: US 8,481,051 B2
(45) Date of Patent: Jul. 9, 2013

(54) CYTOTOXIC T-CELL EPITOPE PEPTIDES THAT SPECIFICALLY ATTACK EPSTEIN-BARR VIRUS-INFECTED CELLS AND USES THEREOF

(75) Inventors: Kiyotaka Kuzushima, Nagoya (JP); Yoshinori Ito, Nagoya (JP); Ayako Okamura, Nagoya (JP); Yoshiki Akatsuka, Nagoya (JP); Yasuo Morishima, Nagoya (JP)

(73) Assignee: Medical and Biological Laboratories Co., Ltd., Nagoya-shi, Aichi (JP)

( * ) Notice: Subject to any disclaimer, the term of this patent is extended or adjusted under 35 U.S.C. 154(b) by 661 days.

(21) Appl. No.: 12/091,705

(22) PCT Filed: Oct. 27, 2006

(86) PCT No.: PCT/JP2006/321479
§ 371 (c)(1),
(2), (4) Date: Aug. 5, 2009

(87) PCT Pub. No.: WO2007/049737
PCT Pub. Date: May 3, 2007

(65) Prior Publication Data
US 2009/0305324 A1 Dec. 10, 2009

(30) Foreign Application Priority Data
Oct. 28, 2005 (JP) ................. 2005-315306

(51) Int. Cl.
*A61K 39/00* (2006.01)
*A61K 38/00* (2006.01)
*C07K 14/00* (2006.01)

(52) U.S. Cl.
USPC ............ 424/230.1; 424/204.1; 424/184.1; 530/350

(58) Field of Classification Search
None
See application file for complete search history.

(56) References Cited

FOREIGN PATENT DOCUMENTS
JP          11-501124 A      1/1999
WO     WO 2004/001424    * 12/2003

OTHER PUBLICATIONS

Attwood, T. The Babel of Bioinformatics, Science (2000) vol. 290, No. 5491, pp. 471-473.*
Baker et al., Protein Structure Predication and Structural Genomics, Science (2001) vol. 294, No. 5540, pp. 93-96.*
Hu, L-F., et al., "Isolation and sequencing of the Epstein-Barr virus BNLF-1 gene (LMP1) from a Chinese nasopharyngeal carcinoma," *Journal of General Virology*, vol. 72(Pt. 10), pp. 2399-2409 (Oct. 1991).
Sample, J., et al., "Epstein-Barr virus types 1 and 2 have nearly identical LMP-1 transforming genes," *Journal of General Virology*, vol. 75(Pt. 10), pp. 2741-2746 (Oct. 1994).
Sandvej, K., et al., "Sequence Analysis of the Epstein-Barr Virus (EBV) Latent Membrane Protein-1 Gene and Promoter Region: Identification of Four Variants Among Wild-Type EBV Isolates," *Blood*, vol. 90(1), pp. 323-330 (Jul. 1, 1997).
Akatsuka, Y., et al., "Efficient cloning and expression of HLA class I cDNA in human B-lymphoblastoid cell lines," *Tissue Antigens*, vol. 59(6), pp. 502-511 (Jun. 2002).
Babcock, G., et al., "The Expression Pattern of Epstein-Barr Virus Latent Genes In Vivo is Dependent upon the Differentiation Stage of the Infected B Cell," *Immunity*, vol. 13(4), pp. 497-506 (Oct. 2000).
Blake, N., et al., "Human CD8$^+$ T Cell Responses to EBV EBNA1: HLA Class I Presentation of the (Gly-Ala)-Containing Protein Requires Exogenous Processing," *Immunity*, vol. 7(6), pp. 791-802 (Dec. 1997).
Bollard, C., et al., "Cytotoxic T Lymphocyte Therapy for Epstein-Barr Virus$^+$ Hodgkin's Disease," *J. Exp. Med.*, vol. 200(12), pp. 1623-1633 (Dec. 20, 2004).
Callan, M.F.C., et al., "Direct Visualization of Antigen-specific CD8$^+$ T Cells during the Primary Immune Response to Epstein-Barr Virus In Vivo," *J. Exp. Med.*, vol. 187(9), pp. 1395-1402 (May 4, 1998).
Comoli, P., et al., "Infusion of autologous Epstein-Barr virus (EBV)-specific cytotoxic T cells for prevention of EBV-related lymphoproliferative disorder in solid organ transplant recipients with evidence of active virus replication," *Blood*, vol. 99(7), pp. 2592-2598 (Apr. 1, 2002).
Dauer, M., et al., "Mature Dendritic Cells Derived from Human Monocytes Within 48 Hours: A Novel Strategy for Dendritic Cell Differentiation from Blood Precursors," *J. Immunol.*, vol. 170(8), pp. 4069-4076 (Apr. 15, 2003).
Demachi-Okamura, A., et al., "Epstein-Barr virus (EBV) latent membrane protein-1-specific cytotoxic T lymphocytes targeting EBV-carrying natural killer cell malignancies," *Eur. J. Immunol.*, vol. 36, pp. 593-602 (Mar. 2006).
Demachi, A., et al., "Characterization of Epstein-Barr Virus (EBV)-Positive NK Cells Isolated from Hydroa Vacciniforme-Like Eruptions," *Microbiol. Immunol.*, vol. 47(7), pp. 543-552 (2003).
Duraiswamy, J., et al., "Therapeutic LMP1 polyepitope vaccine for EBV-associated Hodgkin disease and nasopharyngeal carcinoma," *Blood*, vol. 101(8), pp. 3150-3156 (Apr. 15, 2003, Epub: Dec. 5, 2002)
Duraiswamy, J., et al., "Induction of Therapeutic T-Cell Responses to Subdominant Tumor-associated Viral Oncogene after Immunization with Replication-incompetent Polyepitope Adenovirus Vaccine," *Cancer Res.*, vol. 64(4), pp. 1483-1489 (Feb. 15, 2004).
Heslop, H., et al., "Long-term restoration of immunity against Epstein-Barr virus infection by adoptive transfer of gene-modified virus-specific T lymphocytes," *Nature Medicine*, vol. 2(5), pp. 551-555 (May 1996).

(Continued)

Primary Examiner — Michelle S Horning
(74) *Attorney, Agent, or Firm* — Kilpatrick Townsend & Stockton LLP

(57) ABSTRACT

The present inventors introduced mRNAs for the Epstein-Barr virus proteins LMP1 and EBNA1 into antigen-presenting cells, and as a result, demonstrated that the cells induced Epstein-Barr virus-specific cytotoxic T cells. The present inventors also demonstrated that the cytotoxic T cells recognized epitope peptides presented via HLA-A*0206, HLA-Cw*0303, or HLA-Cw*0304, inhibited the outgrowth of Epstein-Barr virus-infected B cells, and lysed Epstein-Barr virus-infected NK lymphomas and NK cells.

4 Claims, 13 Drawing Sheets

OTHER PUBLICATIONS

Gottschalk, S., et al., "Generating CTLs against the subdominant Epstein-Barr virus LMP1 antigen for the adoptive immunotherapy of EBV-associated malignancies," *Blood*, vol. 101, pp. 1905-1912 (2003).

Kagami, Y., et al., "Establishment of an IL-2-dependent cell line derived from 'nasal-type' NK/T-cell lymphoma of CD2$^+$, sCD3$^-$, CD3ε$^+$, CD56$^+$ phenotype and associated with Epstein-Barr Virus," *British Journal of Haematology*, vol. 103(3), pp. 669-677 (Dec. 1998).

Khanna, R., et al., "Identification of cytotoxic T cell epitopes within Epstein-Barr virus (EBV) oncogene latent membrane protein 1 (LMP1): evidence for HLA A2 supertype-restricted immune recognition of EBV-infected cells by LMP1-specific cytotoxic T lymphocytes," *Eur. J. Immunol.*, vol. 28, pp. 451-458 (1998).

Khanna, R., et al., "Localization of Epstein-Barr Virus Cytotoxic T Cell Epitopes Using Recombinant Vaccinia: Implications for Vaccine Development," *J. Exp. Med.*, vol. 176(1), pp. 169-176 (Jul. 1, 1992).

Khanna, R., et al., "Activation and adoptive transfer of Epstein-Barr virus-specific cytotoxic T cells in solid organ transplant patients with posttransplant lymphoproliferative disease," *Proc. Natl. Acad. Sci. USA*, vol. 96(18), pp. 10391-10396 (Aug. 31, 1999).

Khanna, R., et al., "Isolation of Cytotoxic T Lymphocytes from Healthy Seropositive Individuals specific for Peptide Epitopes from Epstein-Barr Virus Nuclear Antigen 1: Implications for Viral Persistence and Tumor Surveillance," *Virology*, vol. 214(2), pp. 633-637 (Dec. 20, 1995).

Kieff, E., et al., "Epstein-Barr virus and Its Replication," *Fields Virology*, 4th ed., vol. 2, pp. 2511-2573 (2001).

Kimura, H., et al., "Clinical and virologic characteristics of chronic active Epstein-Barr virus infection," *Blood*, vol. 98(2), pp. 280-286 (Jul. 15, 2001).

Kondo, E., et al., "Efficient Generation of Antigen-Specific Cytotoxic T Cells Using Retrovirally Transduced CD40-Activated B Cells," *J. Immunol.*, vol. 169(4), pp. 2164-2171 (Aug. 15, 2002).

Krüger, S., et al., "Identification of a Naturally Processed HLA-DR-Restricted T-Helper Epitope in Epstein-Barr Virus Nuclear Antigen Type 1," *J. Immunother.*, vol. 26(3), pp. 212-221 (May-Jun. 2003).

Kuzushima, et al., "Rapid Determination of Epstein-Barr Virus-Specific CD8$^+$ T-Cell Frequencies by Flow Cytometry," *Blood*, vol. 94(9), pp. 3094-3100 (Nov. 1, 1999).

Lee, S., et al., "CD8 T Cell Recognition of Endogenously Expressed Epstein-Barr Virus Nuclear Antigen 1," *J. Exp. Med.*, vol. 199(10), pp. 1409-1420 (May 17, 2004).

Leen, A., et al., "Differential Immunogenicity of Epstein-Barr Virus Latent-Cycle Proteins for Human CD4$^+$ T-Helper 1 Responses," *J. Virol.*, vol. 75(18), pp. 8649-8659 (Sep. 2001).

Levitskaya, J., et al., "Inhibition of antigen processing by the internal repeat region of the Epstein-Barr virus nuclear antigen-1," *Nature*, vol. 375(6533), pp. 685-688 (Jun. 22, 1995).

Levitskaya, J., et al., "Inhibition of ubiquitin/proteasome-dependent protein degradation by the Gly-Ala repeat domain of the Epstein-Barr virus nuclear antigen 1," *Proc. Natl. Acad. Sci. USA*, vol. 94(23), pp. 12616-12621 (Nov. 11, 1997).

Lin, C-L, et al., "Immunization with Epstein-Barr Virus (EBV) Peptide-pulsed Dendritic Cells Induces Functional CD8+ T-Cell Immunity and May Lead to Tumor Regression in Patients with EBV-positive Nasopharyngeal Carcinoma," *Cancer Res.*, vol. 62(23), pp. 6952-6958 (Dec. 1, 2002).

Murray, R.J., et al., "Identification of Target Antigens for the Human Cytotoxic T Cell Response to Epstein-Barr Virus (EBV): Implications for the Immune Control of EBV-positive Malignancies," *J. Exp. Med.*, vol. 176(1), pp. 157-168 (Jul. 1, 1992).

Nagata, H., et al., "Characterization of novel natural killer (NK)-cell and γδ T-cell lines established from primary lesions of nasal T/NK-cell lymphomas associated with Epstein-Barr virus," *Blood*, vol. 97(3), pp. 708-713 (Feb. 1, 2001).

Paludan, et al., "Epstein-Barr Nuclear Antigen 1-Specific CD4$^+$ Th1 Cells Kill Burkitt's Lymphoma Cells," *J. Immunol.*, vol. 169(3), pp. 1593-1603 (Aug. 1, 2002).

Rickinson, A., et al., "Epstein-Barr Virus," *Fields Virology*, 4th ed., vol. 2, pp. 2575-2627 (2001).

Rooney, C., et al., "Infusion of Cytotoxic T Cells for the Prevention and Treatment of Epstein-Barr Virus-Induced Lymphoma in Allogeneic Transplant Recipients," *Blood*, vol. 92(5), pp. 1549-1555 (Sep. 1, 1998).

Rooney, C., et al., "Use of gene-modified virus-specific T lymphocytes to control Epstein-Barr-virus-related lymphoproliferation," *Lancet*, vol. 345(8941), pp. 9-13 (Jan. 7, 1995).

Steven, N., et al., "Epitope Focusing in the Primary Cytotoxic T Cell Response to Epstein-Barr-Virus and Its Relationship to T Cell Memory," *J. Exp. Med.*, vol. 184(5), pp. 1801-1813 (Nov. 1, 1996).

Straathof, K., et al., "Treatment of nasopharyngeal carcinoma with Epstein-Barr virus-specific T lymphocytes," *Blood*, vol. 105(5), pp. 1898-1904 (Mar. 1, 2005, Epub: Nov. 12, 2004).

Tellam, et al., "Endogenous Presentation of CD8$^+$ T Cell Epitopes from Epstein-Barr Virus-encoded Nuclear Antigen 1," *J. Exp. Med.*, vol. 199(10), pp. 1421-1431 (May 17, 2004).

Voo, K., et al., "Identification of HLA-DP3-restricted Peptides from EBNA1 Recognized by CD4$^+$ T Cells," *Cancer Res.*, vol. 62(24), pp. 7195-7199 (Dec. 15, 2002).

Voo, K., et al., "Evidence for the Presentation of Major Histocompatability Complex Class I-restricted Epstein-Barr Virus Antigen 1 Peptides to CD8$^+$ T Lymphocytes," *J. Exp. Med.*, vol. 199(4), pp. 459-470 (Feb. 16, 2004, Epub: Feb. 9, 2004).

Yin, Y., et al., "Self-Inhibition of Synthesis and Antigen Presentation by Epstein-Barr Virus-Encoded EBNA1," *Science*, vol. 307(5638), pp. 1371-1374 (Sep. 5, 2003).

Zhang, Y., et al., "Common cytological and cytogenetic features of Epstein-Barr virus (EBV)-positive natural killer (NK) cells and cell lines derived from patients with nasal T/NK-cell lymphomas, chronic active EBV infection and hydroa vacciniforme-like eruptions," *British Journal of Haematology*, vol. 121(5), pp. 805-814 (Jun. 2003).

\* cited by examiner

A

PEPTIDE #24: RRPFF<u>HPVGEADYFEY</u>HQEG  (SEQ ID
                402                              421    NO: 19)

B

PEPTIDE #38: EGTWVAG<u>VFVYGGSKTSLYN</u>  (SEQ ID
                500        507                519    NO: 20)

PEPTIDE #39: <u>VFVYGGSKTSLYN</u>LRRGTAL  (SEQ ID
                507              519       526    NO: 21)

11-MER: VFVYGGSKTSL  (SEQ ID NO: 2)
        507       517

10-MER: FVYGGSKTSL  (SEQ ID NO: 3)
        508      517

FIG. 10 (A-B)

CYTOTOXIC T-CELL EPITOPE PEPTIDES THAT SPECIFICALLY ATTACK EPSTEIN-BARR VIRUS-INFECTED CELLS AND USES THEREOF

CROSS-REFERENCES TO RELATED APPLICATIONS

This application is a U.S. National Phase of PCT/JP2006/321479, filed Oct. 27, 2006, which claims priority to Japanese Patent Application No. 2005-315306, filed Oct. 28, 2005, the contents of which are herein incorporated by reference.

TECHNICAL FIELD

The present invention relates to Epstein-Barr virus-specific cytotoxic T cell epitope peptides, vaccines using such peptides for treating or preventing Epstein-Barr virus infection or Epstein-Barr virus-positive cancers, and passive immunotherapeutic agents against Epstein-Barr virus

BACKGROUND ART

The Epstein-Barr virus (a γ herpes virus that stays dormant (latent) for a long period in memory B cells; hereinafter may be abbreviated as EBV) is involved in many malignancies, for example, Burkitt's lymphoma, Hodgkin's disease (HD) and nasopharyngeal carcinoma (NPC), as well as post-transplant lymphoproliferative disorder (Non-patent Document 1). In latent infections, viral protein expression is suppressed. All EBV-positive malignant cells exhibit one of the following three latency types. These types are distinguished from each other by the EBV antigen expression patterns (Non-patent Document 2).

Latency type I: only EBV nuclear antigen (EBNA) 1 is expressed in Burkitt's lymphoma.

Latency type II: latent membrane protein 1 (hereinafter abbreviated as LMP1) and LMP2, as well as EBNA1, are expressed in Hodgkin's disease and nasopharyngeal carcinoma.

Latency type III: all EBV latent proteins, i.e., EBNA1, EBNA2, EBNA3A, EBNA3B, EBNA3C, leader protein, LMP1, and LMP2 are expressed in post-transplant lymphoproliferative disorder.

There is increasing interest in using immunotherapy for EBV-associated malignancies. Adoptive immunotherapy using in vitro-activated EBV-specific cytotoxic T lymphocytes (hereinafter may be abbreviated as CTLs) has proven effective for prevention and treatment of EBV-associated lymphoproliferative disorders following hematopoietic stem cell or organ transplantation (Non-patent Documents 3-7). Application of a similar strategy to other EBV-associated malignancies such as Hodgkin's disease (Non-patent Document 8) and nasopharyngeal carcinoma (Non-patent Document 9) has been reported to be effective in some patients. However, the majority of lymphoblastoid cell line (hereinafter abbreviated as LCL)-activated CTLs used in these studies were directed to EBNA3A, EBNA3B, and EBNA3C, which antigens are not expressed in malignant tumors such as Hodgkin's disease and nasopharyngeal carcinoma. A portion of LCL-activated CTLs might recognize peptides derived from LMP2 and contribute to immunotherapeutic effects in patients (Non-patent Documents 8-9). However, T cells directed to LMP1 peptides are very rare, reflecting low frequency of LMP1 peptide-specific CTL precursor cells (Non-patent Document 10). To selectively activate T cells specific to subdominant EBV antigens, Lin et al. used monocyte-derived dendritic cells (DCs) pulsed with LMP2-derived peptides to immunize NPC patients (Non-patent Document 11). Some methods for activating LMP1-specific CTLs have also been reported. Khanna et al. first described HLA-A2-restricted LMP1 epitopes and induction of CTLs using antigen-presenting cells (APCs) pulsed with the peptides (Non-patent Document 10). They also utilized a replication-incompetent adenovirus and a recombinant vaccinia virus encoding multiple LMP1 epitopes, successfully immunizing HLA-A2 transgenic mice, and achieving inhibition of the growth of LMP1 gene-transduced cells (Non-patent Documents 12-13). Gottschalk et al. reported the induction of polyclonal LMP1-specific CTLs using dendritic cells infected with a recombinant adenovirus expressing an N-terminal-truncated, non-toxic LMP1 mutant (Non-patent Document 14).

One category of EBV-associated malignancies is EBV infection in NK/T cells (Non-patent Document 1). Chronic active EBV infection (CAEBV) is another disorder whereby EBV infects mainly NK/T cells to cause life-threatening lymphoproliferative disease (Non-patent Document 15). EBV-positive NK/T cell malignancies express EBNA1 and LMP1 as potential CTL targets (Non-patent Documents 15-17).

LMP1 is a transmembrane oncoprotein that enhances cell survival through upregulation of anti-apoptotic genes (Non-patent Document 2). Expression of LMP1 is essential for growth transformation of human B-lymphocytes and is necessary for the proliferation of EBV-infected human monocytes (Non-patent Document 2). LMP1 has also been known to induce tumorigenic transformation of the murine cell line BALB/c3T3 and B cell lymphomas. Moreover, LMP1 expression might be important for the proliferative capacity of EBV-infected NK cells (Non-patent Document 18). However, it has not been demonstrated that such NK/T cells can process LMP1 and generate HLA-restricted epitopes.

EBNA1 is required for the maintenance and replication of viral plasmids in EBV-transformed cells (Non-patent Document 19). Because EBNA1 is expressed in all EBV-associated tumors, it is an attractive target for immunotherapy. However, CD8$^+$ CTL responses are preferentially directed toward EBNA3A, EBNA3B, and EBNA3C among latent antigens, and EBNA1 has been believed to be not recognized by CTLs and thus to be immunologically undetectable (Non-patent Documents 20-23). A glycine-alanine repeat sequence (GAr) within EBNA1 was found to prevent antigen processing for CTL recognition (Non-patent Document 24). Presence of this GAr proved to prevent processing by proteasomes, the main catalytic machinery for generating MHC class I epitopes (Non-patent Documents 25-26). Moreover, the very same domain was found to prevent EBNA1 mRNA translation (Non-patent Document 27).

EBV-specific CD4$^+$ T cell responses have been examined and it has been elucidated that EBNA 1-specific CD4$^+$ T cell responses are seen mainly in helper T cell type 1 that directly recognizes EBV-infected cells. Several MHC class II-restricted EBNA1 epitopes have been identified (Non-patent Documents 28-32), implying that EBNA1-specific CD4$^+$ T cells may play a role in controlling tumor growth in vivo. Surprisingly, very recent studies demonstrated EBNA1-specific CD8$^+$ CTLs to moderately lyse EBV-infected lymphoblastoid cell lines (LCLs) and suppress LCL outgrowth in vivo (Non-patent Documents 33-35). However, only a small number of EBNA1 epitopes that activate CD8$^+$ CTLs have been identified so far.

Induction of CTLs with very few precursor cells has been tried by immunologists as well as clinicians anticipating tumor-associated antigen-targeted immunotherapy. Antigen-presenting cells transduced with in vitro-transcribed mRNA encoding specific antigens can induce CTLs specific to tumor-associated antigens, or to self antigens, overcoming immunological tolerance (Non-patent Documents 36-40). The above methods have the following advantages:
(1) complete loss of antigenicity of vector backbone sequences;
(2) highly reproducible yields with in vitro transcription; and
(3) high efficiency of transduction using electroporation.

Namely, it is inferred that antigen-presenting cells transduced with mRNA of EBV antigens (epitopes) might be suitable for induction of EBV-specific CTLs. To realize the above methods, identification of CTL epitope peptides specific to EBV was needed.

Prior art documents related to the present invention described in this application include:
Non-patent Document 1: Babcock G. J., et al., Immunity, 13:497-506 (2000)
Non-patent Document 2: Rickinson A. B., et al., In: Knipe D. M., Howley P. M., eds. Fields Virology (ed Fourth Edition), Philadelphia, Lippincott Williams & Wilkins, 2575:2628 (2001)
Non-patent Document 3: Rooney C. M., et al., Lancet, 345: 9-13 (1995)
Non-patent Document 4: Heslop H. E., et al., Nat. Med., 2:551-555 (1996)
Non-patent Document 5: Rooney C. M., et al., Blood, 92:1549-1555 (1998)
Non-patent Document 6: Khanna R., et al., Proc. Natl. Acad. Sci. USA, 96:10391-10396 (1999)
Non-patent Document 7: Comoli P., et al., Blood, 99:2592-2598 (2002)
Non-patent Document 8: Bollard C. M., et al., J. Exp. Med., 200:1623-1633 (2004)
Non-patent Document 9: Straathof K. C., et al., Blood, 105: 1898-1904 (2005)
Non-patent Document 10: Khanna R., et al., Eur. J. Immunol., 28:451-458 (1998)
Non-patent Document 11: Lin C. L., et al., Cancer Res., 62:6952-6958 (2002)
Non-patent Document 12: Duraiswamy J., et al., Blood, 101: 3150-3156 (2003)
Non-patent Document 13: Duraiswamy J., et al., Cancer Res., 64:1483-1489 (2004)
Non-patent Document 14: Gottschalk S., et al., Blood, 101: 1905-1912 (2003)
Non-patent Document 15: Kimura H., et al., Blood, 98:280-286 (2001)
Non-patent Document 16: Nagata H., et al., Blood, 97:708-713 (2001)
Non-patent Document 17: Zhang Y., et al., Br. J. Haematol., 121:805-814 (2003)
Non-patent Document 18: Demachi A., et al., Microbiol. Immunol., 47:543-52 (2003)
Non-patent Document 19: Kieff E., et al., In: Knipe D. M., Howley P. M., eds. Fields Virology (ed Fourth Edition), Philadelphia, Lippincott Williams & Wilkins, 2511-2574 (2001)
Non-patent Document 20: Khanna R., et al., J. Exp. Med., 176:169-176 (1992)
Non-patent Document 21: Murray R. J., et al., J. Exp. Med., 176:157-168 (1992)
Non-patent Document 22: Steven N. M., et al., J. Exp. Med., 184:1801-1813 (1996)
Non-patent Document 23: Callan M. F., et al., J. Exp. Med., 187:1395-1402 (1998)
Non-patent Document 24: Levitskaya J., et al., Nature, 375: 685-688 (1995)
Non-patent Document 25: Blake N., et al., Immunity, 7:791-802 (1997)
Non-patent Document 26: Levitskaya J., et al., Proc. Natl. Acad. Sci. USA, 94:12616-12621 (1997)
Non-patent Document 27: Yin Y., et al., Science, 301:1371-1374 (2003)
Non-patent Document 28: Khanna R., et al., Virology, 214: 633-637 (1995)
Non-patent Document 29: Leen A., et al., J. Virol., 75:8649-8659 (2001)
Non-patent Document 30: Paludan C., et al., J. Immunol., 169:1593-1603 (2002)
Non-patent Document 31: Voo K. S., et al., Cancer Res., 62:7195-7199 (2002)
Non-patent Document 32: Kruger S., et al., J. Immunother., 26:212-221 (2003)
Non-patent Document 33: Lee S. P., et al., J. Exp. Med., 199:1409-1420 (2004)
Non-patent Document 34: Tellam J., et al., J. Exp. Med., 199:1421-1431 (2004)
Non-patent Document 35: Voo K. S., et al., J. Exp. Med., 199:459-470 (2004)
Non-patent Document 36: Kuzushima K., et al., Blood, 94:3094-3100 (1999)
Non-patent Document 37: Kagami Y., et al., Br. J. Haematol., 103:669-677 (1998)
Non-patent Document 38: Akatsuka Y., et al., Tissue Antigens, 59:502-511 (2002)
Non-patent Document 39: Kondo E., et al., J. Immunol., 169:2164-2171 (2002)
Non-patent Document 40: Dauer M., et al., J. Immunol., 170:4069-4076 (2003)

DISCLOSURE OF THE INVENTION

Problems to be Solved by the Invention

The present invention was achieved in view of the above circumstances. An objective of the present invention is to provide EBV-specific CTL epitope peptides, vaccines for treating or preventing EBV infection using such peptides, passive immunotherapeutic agents against EBV, and methods for quantifying EBV-specific CTLs.

Means for Solving the Problems

To achieve the above objective, the present inventors introduced mRNAs for EBV proteins LMP1 and EBNA1 into antigen-presenting cells, and assessed the antigen-presenting cells for the ability to induce EBV-specific CTLs.

The result showed that antigen-presenting cells expressing the EBV proteins stimulated CTLs derived from healthy persons, and the CTLs inhibited the growth of EBV-infected B cells and lysed EBV-infected NK lymphoma and NK cells. In addition, the CTLs were demonstrated to recognize epitope peptides presented via the HLA-A*0206, HLA-Cw*0303, or HLA-Cw*0304 molecule.

Specifically, the present inventors succeeded in identifying EBV-specific CTL epitope peptides, and thus completed the present invention.

More specifically, the present invention provides:
[1] an Epstein-Barr virus-specific cytotoxic T cell epitope peptide;
[2] the peptide of [1], wherein the Epstein-Barr virus-specific cytotoxic T cell epitope peptide comprises at least one amino acid sequence selected from the group consisting of SEQ ID NOs: 1 to 3;

[3] the peptide of [1] comprising an amino acid sequence with a substitution, deletion, insertion, and/or addition of one or more amino acids in the amino acid sequence of any one of SEQ ID NOs: 1 to 3, which has a function capable of inducing an Epstein-Barr virus-specific cytotoxic T cell;

[4] the peptide of any one of [1] to [3], wherein the peptide comprises an antigen peptide restricted by HLA-A*0206, HLA-Cw*0303, or HLA-Cw*0304 molecule and has a function capable of inducing a cytotoxic T cell having a T cell receptor capable of specifically recognizing a cell that presents a complex with HLA-A*0206, HLA-Cw*0303, or HLA-Cw*0304 molecule on the cell surface;

[5] a nucleic acid encoding the peptide of any one of [1] to [4];

[6] a vaccine for treating or preventing Epstein-Barr virus infection, which comprises as an active ingredient the peptide of any one of [1] to [4];

[7] a vaccine for treating or preventing Epstein-Barr virus infection, which comprises as an active ingredient the nucleic acid of [5];

[8] a vaccine for treating or preventing Epstein-Barr virus infection, which comprises as an active ingredient an antigen-presenting cell that presents the peptide of any one of [1] to [4] by HLA;

[9] a passive immunotherapeutic agent against Epstein-Barr virus, which comprises as an active ingredient an Epstein-Barr virus-specific cytotoxic T cell obtained by stimulating a peripheral blood lymphocyte with the peptide of any one of [1] to [4] or an antigen-presenting cell that presents said peptide by HLA;

[10] a passive immunotherapeutic agent against Epstein-Barr virus, which comprises as an active ingredient a cytotoxic T cell that is obtained by reacting a peripheral blood lymphocyte with a major histocompatibility antigen complex and/or major histocompatibility antigen complex-tetramer prepared from the peptide of any one of [1] to [4], allowing the formation of a complex in which said major histocompatibility antigen complex and/or major histocompatibility antigen complex-tetramer are bound with a cytotoxic T cell, and isolating the cytotoxic T cell from said complex;

[11] a method for inducing a cytotoxic T cell, which comprises inducing a cytotoxic T cell using the peptide of any one of [1] to [4];

[12] the method of [11], wherein an Epstein-Barr virus-specific cytotoxic T cell is induced by contacting the peptide of any one of [1] to [4] with a peripheral blood mononuclear cell in a culture medium containing plasma;

[13] a method for producing a passive immunotherapeutic agent against Epstein-Barr virus, which comprises the step of obtaining an Epstein-Barr virus-specific cytotoxic T cell by stimulating a peripheral blood lymphocyte with the peptide of any one of [1] to [4] or an antigen-presenting cell that presents said peptide by HLA;

[14] a method for producing a passive immunotherapeutic agent against Epstein-Barr virus, which comprises the step of obtaining a cytotoxic T cell by reacting a peripheral blood lymphocyte with a major histocompatibility antigen complex and/or major histocompatibility antigen complex-tetramer prepared from the peptide of any one of [1] to [4], allowing the formation of a complex in which said major histocompatibility antigen complex and/or major histocompatibility antigen complex-tetramer are bound with the cytotoxic T cell, and isolating the cytotoxic T cell from said complex;

[15] a method for quantifying Epstein-Barr virus-specific cytotoxic T cells, which comprises: stimulating a peripheral blood with the peptide of any one of [1] to [4], obtaining cytotoxic T cells specific to said virus, and assaying a cytokine and/or chemokine and/or cell surface molecule produced by the cytotoxic T cells; and

[16] a method for quantifying Epstein-Barr virus-specific cytotoxic T cells in peripheral blood, which comprises: preparing a major histocompatibility antigen complex-tetramer and reacting peripheral blood with the major histocompatibility antigen complex-tetramer.

A: Dendritic cells (DC) and CD40-B cells (CD40-B) were transduced with ΔLMP1 mRNA and analyzed for expression of ΔLMP1 by flow cytometry. The dotted lines show cells not transduced with the gene and the solid lines show ΔLMP1-transduced cells.

B: Peripheral $CD8^+$ T cells were stimulated three times with irradiated, autologous ΔLMP1 mRNA-transduced antigen-presenting cells and assayed by ELISPOT using ΔLMP1 mRNA-transduced or non-transduced CD40-B cells as antigen-presenting cells. Data show the number of spots per 500 $CD8^+$ T cells.

C: Six kinds of antigen-presenting cells were prepared by transducing fully HLA-mismatched LCL cells with each HLA gene derived from donors. A CTL clone, H7, was stimulated and IFNγ production was tested by ELISPOT assay. One-thousand H7 cells were placed per well.

Figure 2:
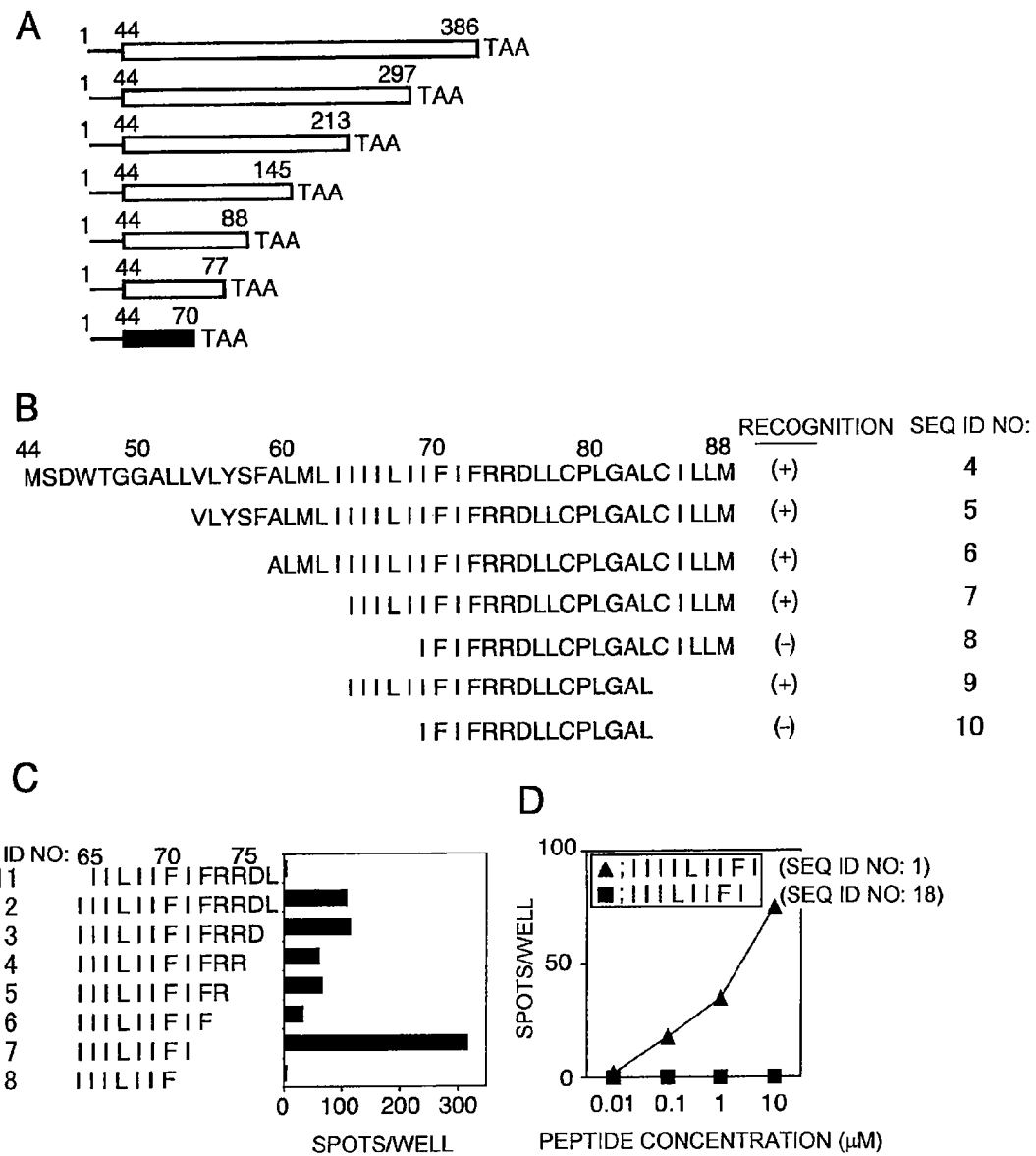

FIG. 2 shows LMP1 epitope peptides recognized by the H7 CTL clone.

A: A series of C-terminal-truncated ΔLMP1 mRNAs were generated by in vitro transcription. A methionine at amino acid position 44 was used as the start codon for each mRNA. CD40-B cells transduced with each C-terminal-truncated ΔLMP1 mRNA were used as antigen-presenting cells in the ELISPOT assay. The mRNA fragments shown as open boxes were recognized by H7 cells, while the mRNA fragments shown as filled box were not.

B: A series of C- and T-terminal truncated fragments were amplified by PCR and cloned into the pcDNA3.1 (+) vector. The predicted amino acid sequences encoded by the transduced DNAs are shown. H7 cell recognition of A0206-293T cells transfected with each plasmid was determined by ELISPOT assay (1,000H7 cells/well) and categorized into two patterns as follows depending on the number of IFNγ spots: (+), 50 or more spots; (−), less than 10 spots.

C: The number of IFNγ spots of H7 cells stimulated with A0206-293T cells transduced with each gene are shown. Each bar represents the number of spots per 1,000H7 cells.

D: ELISPOT assays were performed using A0206-293T cells pulsed with various concentrations of synthetic peptides. Data show the number of spots per 500H7 cells.

Figure 3:
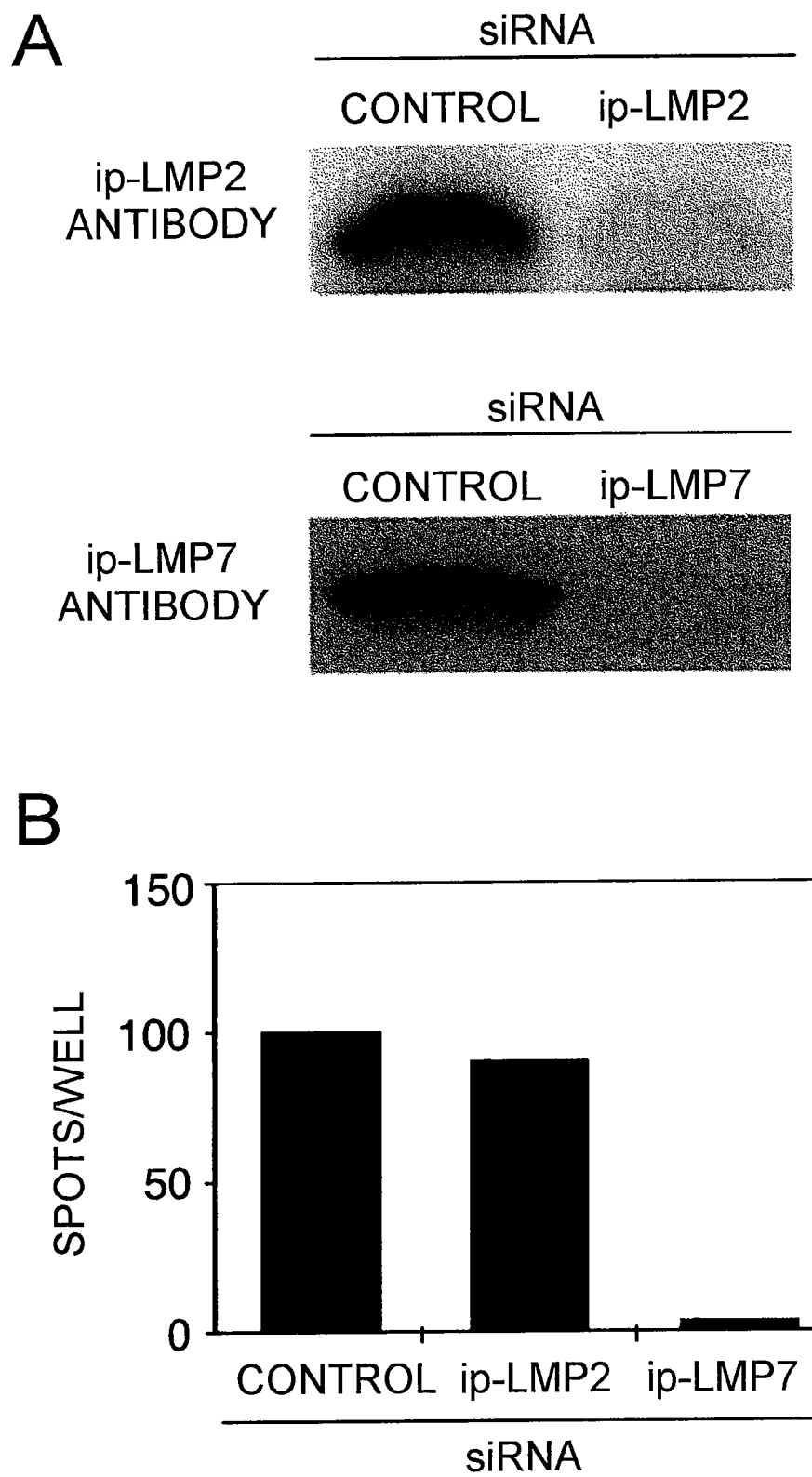

FIG. 3 shows the result of an analysis done on importance of ip-LMP7 in LMP1 epitope processing.

A: Control siRNA, ip-LMP2 siRNA, or ip-LMP7 siRNA was retrovirally transduced into autologous LCLs. The cells were selected for 14 days with puromycin, followed by Western blot analysis of ip-LMP2 (upper panel) and ip-LMP7 (lower panel).

B: ELISPOT assays were performed using ip-LMP2- or ip-LMP7-silenced autologous LCLs. IFNγ spot production of H7 was estimated. Each bar represents the number of spots per 5,000H7 cells.

Figure 4:
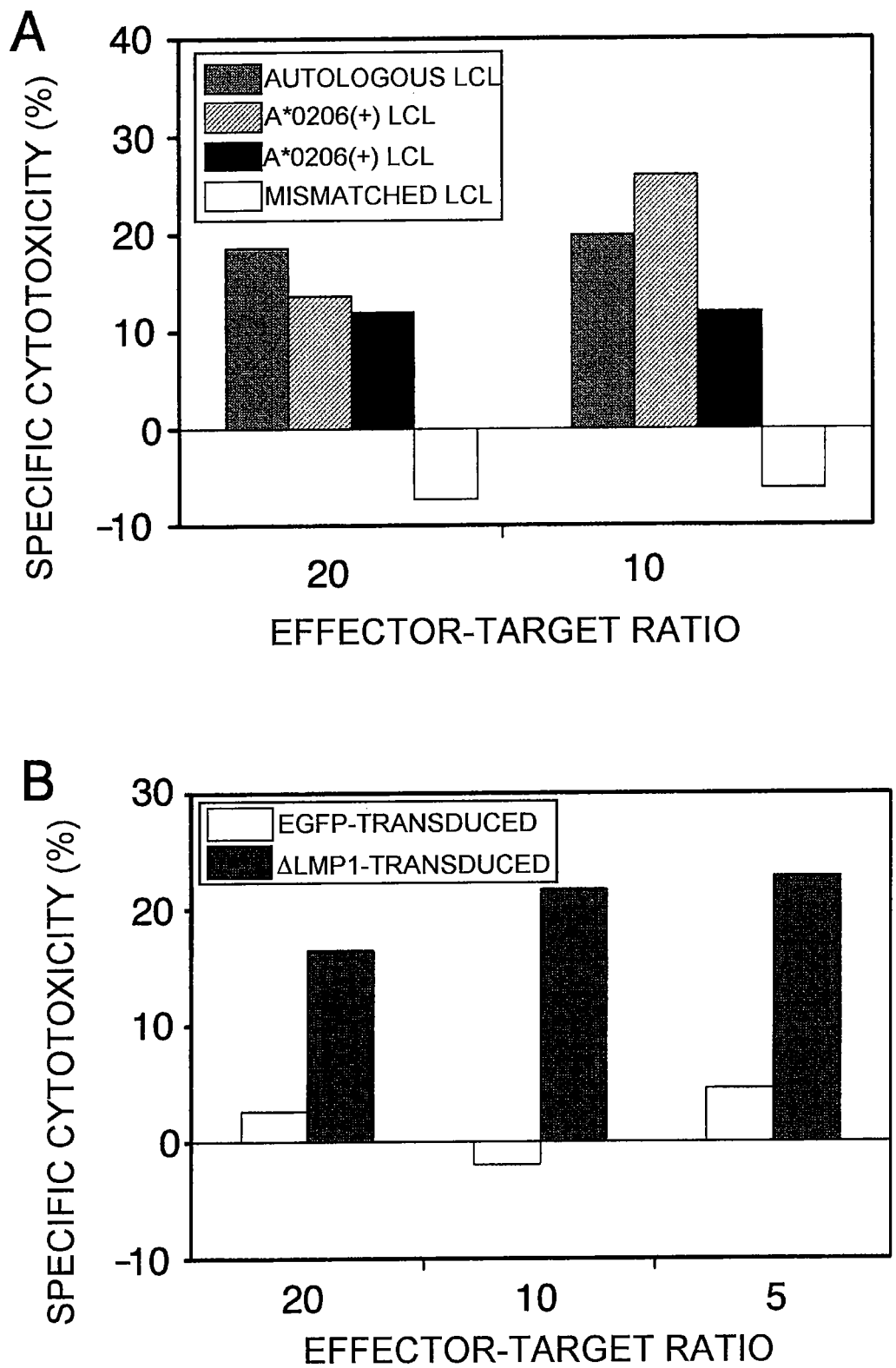

FIG. 4 shows cytotoxic activity of the LMP1-specific CTL clone, H7.

A: Sixteen-hour CTL assays were performed using autologous, A*0206-shared, and fully HLA-mismatched LCLs as target cells.

B: Four-hour CTL assays were performed using ΔLMP1- or EGFP-transduced LCLs as target cells. Each bar represents the mean cytotoxic activity in triplicate wells.

Figure 5:
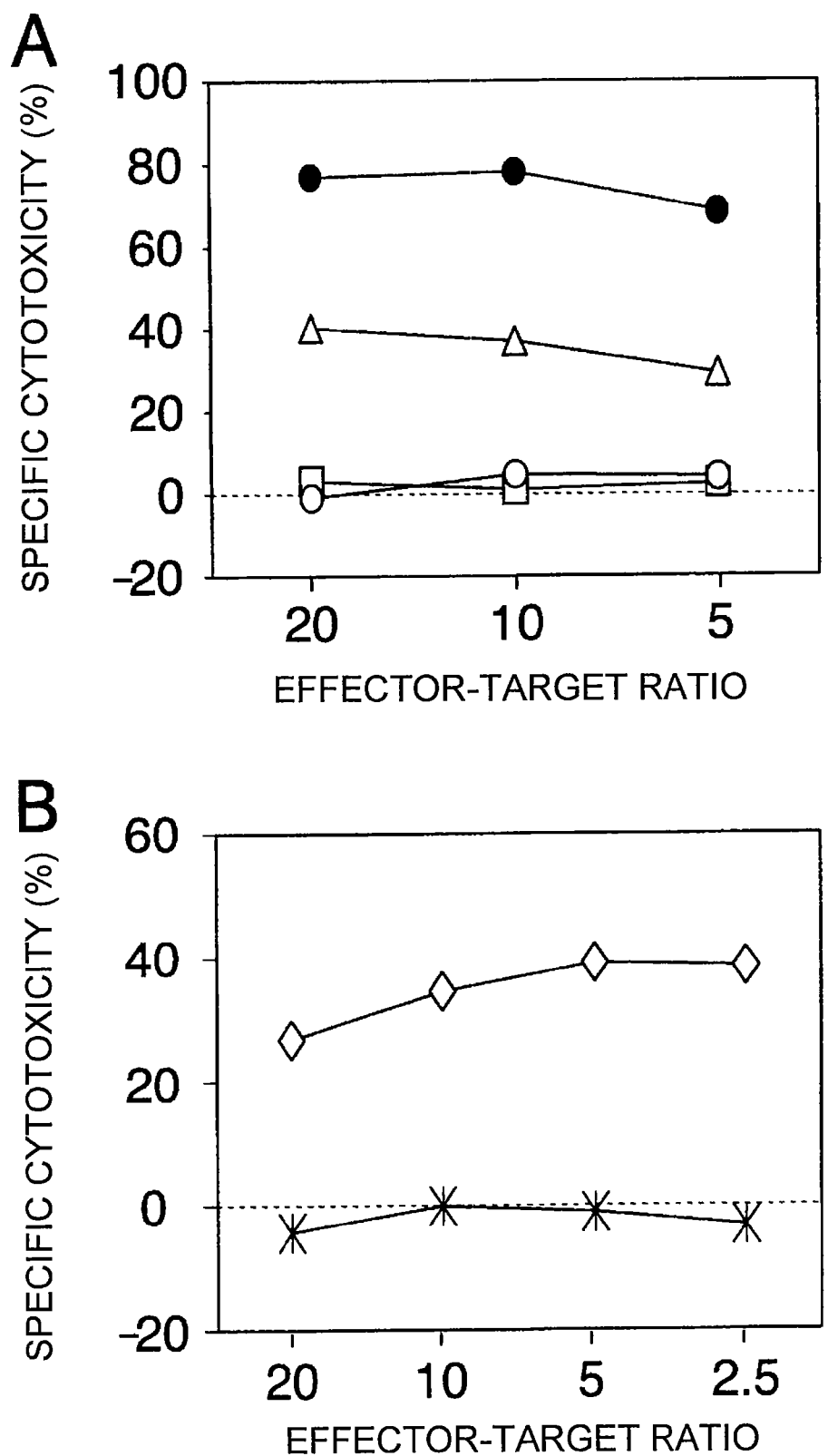

FIG. 5 shows EBV-positive NK cell line-specific lysis by CTLs.

A: Cytotoxic activity of the CTL clone, H7, against EBV-positive NK cell lines was assessed in 16-hour CTL assays. Data for two HLA-A*0206-positive NK cell lines (SNK-6 and SNK-10) and one A*0206-negative NK cell line (HANK-1) are shown with open circles, open triangles, and open squares, respectively. Cytotoxic activity measured in four-hour CTL assays using SNK-6 cell pulsed with 100 nM epitope peptide is shown with solid circles.

B: Sixteen-hour CTL assays were performed using HLA-A*0206-transduced (diamonds) or A*2402-transduced (asterisks) HANK-1 cells.

Figure 6:
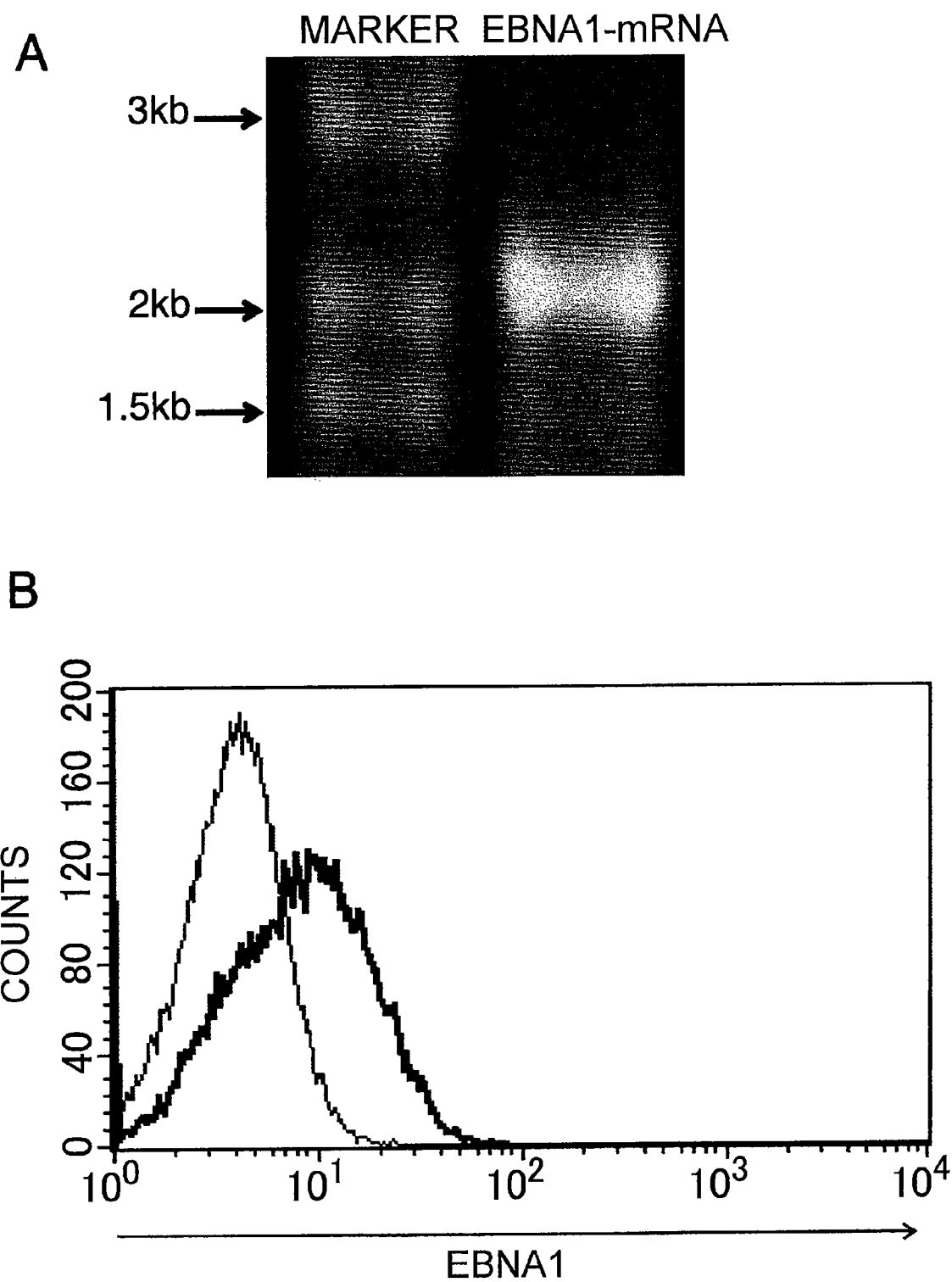

FIG. 6 shows EBNA1 expression in cells transduced with in vitro-transcribed full-length EBNA1 mRNA.

A: In vitro-transcribed full-length EBNA1 mRNA was produced from an EBNA1 cDNA plasmid. The EBNA1 mRNA was stained with ethidium bromide and assessed by gel electrophoresis.

B: EBNA1 protein expression in EBNA1 mRNA-transduced CD40-B cells. CD40-B cells were transduced with full-length EBNA1 mRNA by electroporation and intracellular staining of EBNA1 protein was performed and analyzed by flow cytometry.

Figure 7:
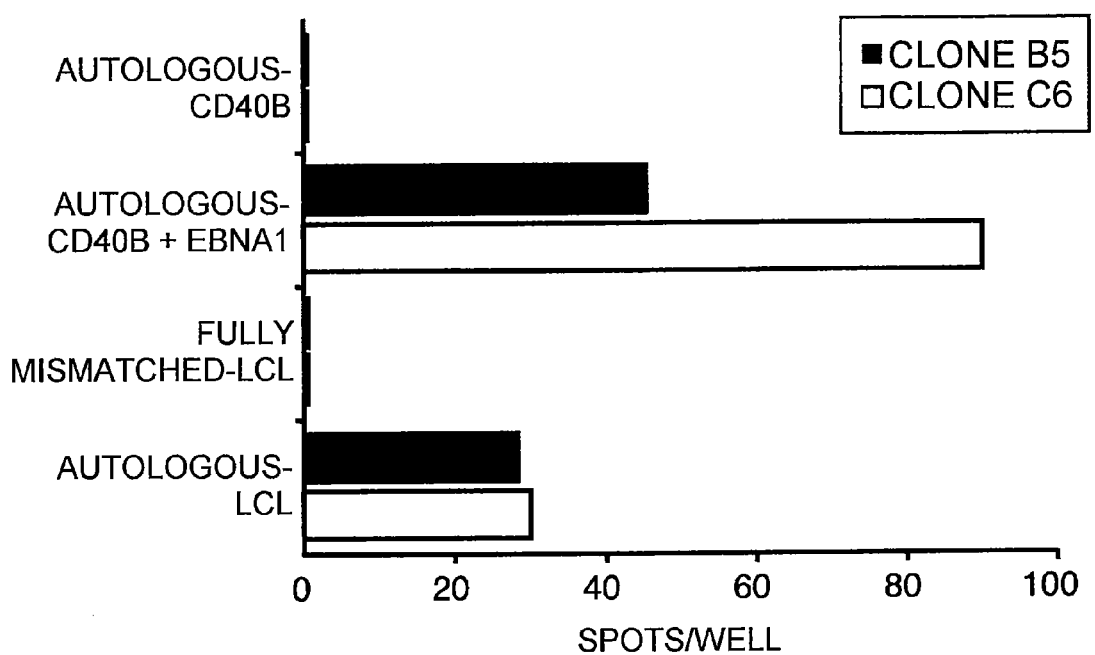

FIG. 7 shows the presence of anti-EBNA1 T cells in culture media primed with EBNA1 mRNA-transduced dendritic cells. CD8+ T cells from a healthy donor were stimulated with autologous dendritic cells transduced with in vitro-transcribed EBNA1 mRNA. After three times of stimulation at weekly intervals, polyclonal CD8+ T cells from two positive culture media were cloned by limiting dilution. Established clones B5 and C6 were then tested for recognition of EBNA1 mRNA-transfected autologous CD40-B cells and autologous LCLs by ELISPOT assay. Five-thousand CTLs were seeded in each well. Data from one representative experiment out of two are shown.

Figure 8:
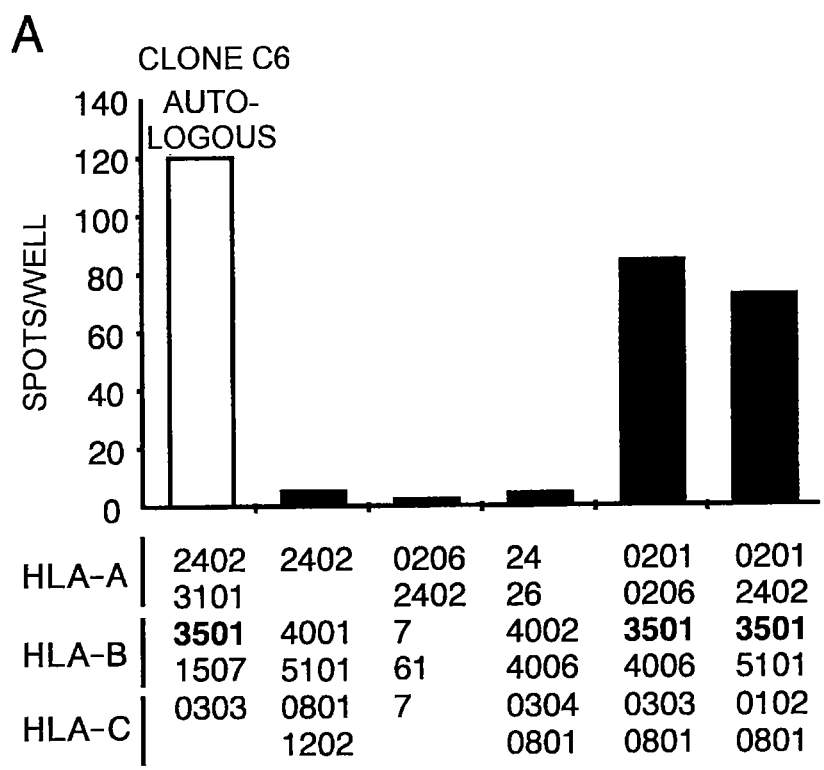
Figure 8:
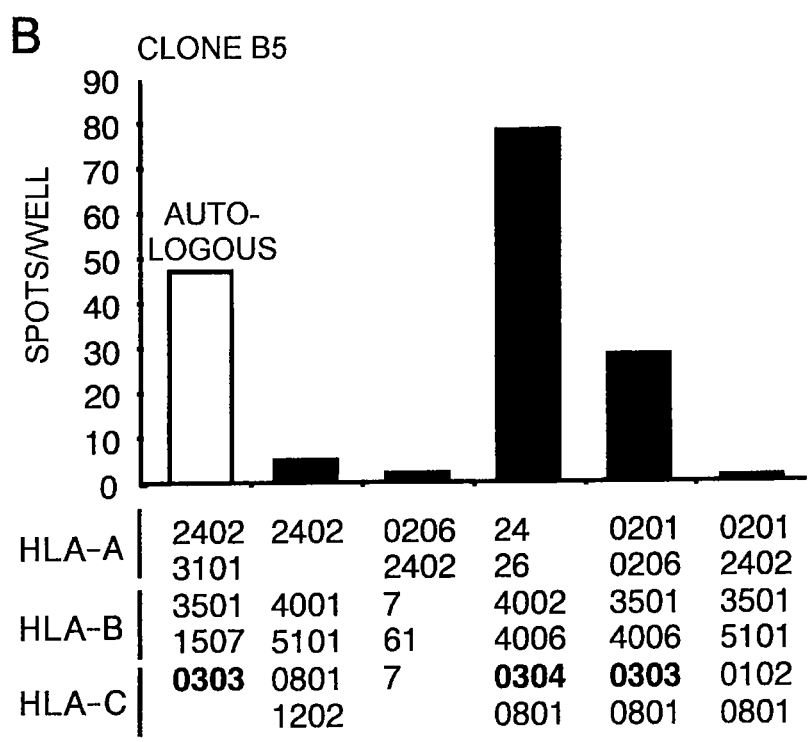

FIG. 8 shows the identification of HLA molecules presented for EBNA1-specific CTL clones.

A: HLA-B*3501 molecule functions as a restriction molecule for CTL clone C6.

B: HLA-Cw*0303 and Cw*0304 molecules function as restriction molecules for CTL clone B5. Autologous and allogenic LCLs were used as antigen-presenting cells for production of IFNγ spots by B5 or C6 clones. Each LCL was cultured with 5×10³ CTLs for 20 hours. Each bar represents the mean number of spots in duplicate wells.

Figure 9:
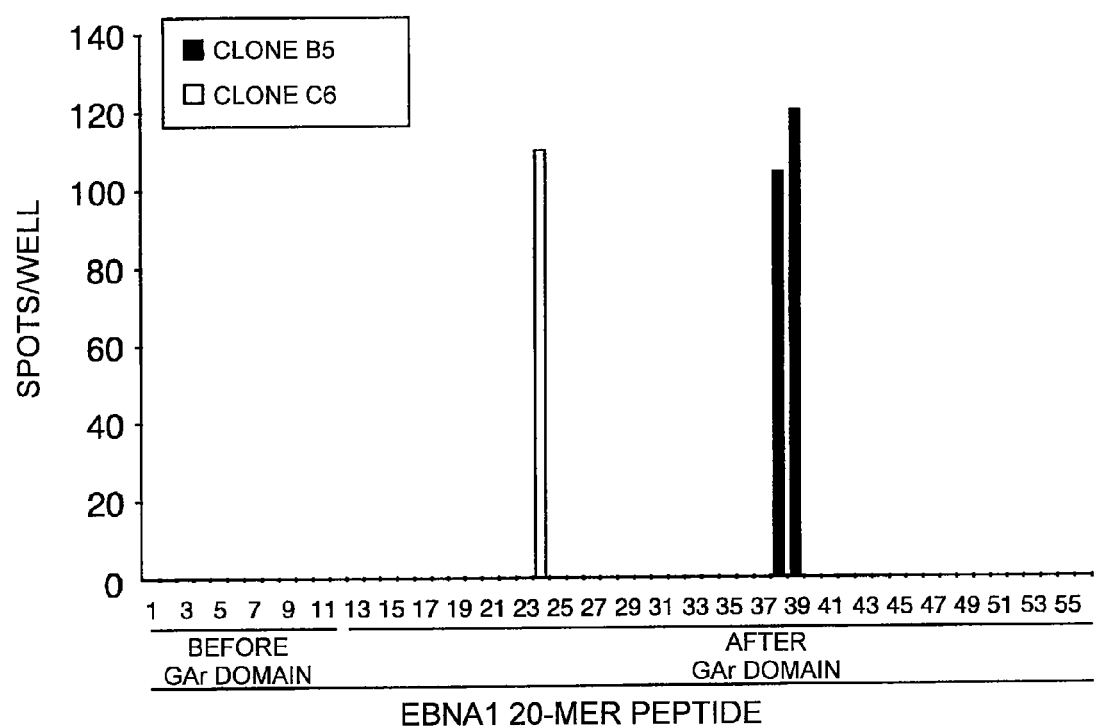

FIG. 9 shows the identification of overlapping peptides recognized by EBNA1-specific CTL clones. Autologous CD40-B cells (1×10⁵/well) were pulsed with 10 μg/mL each of a set of 20-mer overlapping peptides encompassing the whole amino acid sequence of the EBNA1 protein excluding the GAr domain, and co-cultured with 5×10² CTL clones B5 or C6. Production of IFNγ spots was then measured by ELISPOT assays.

Figure 10:
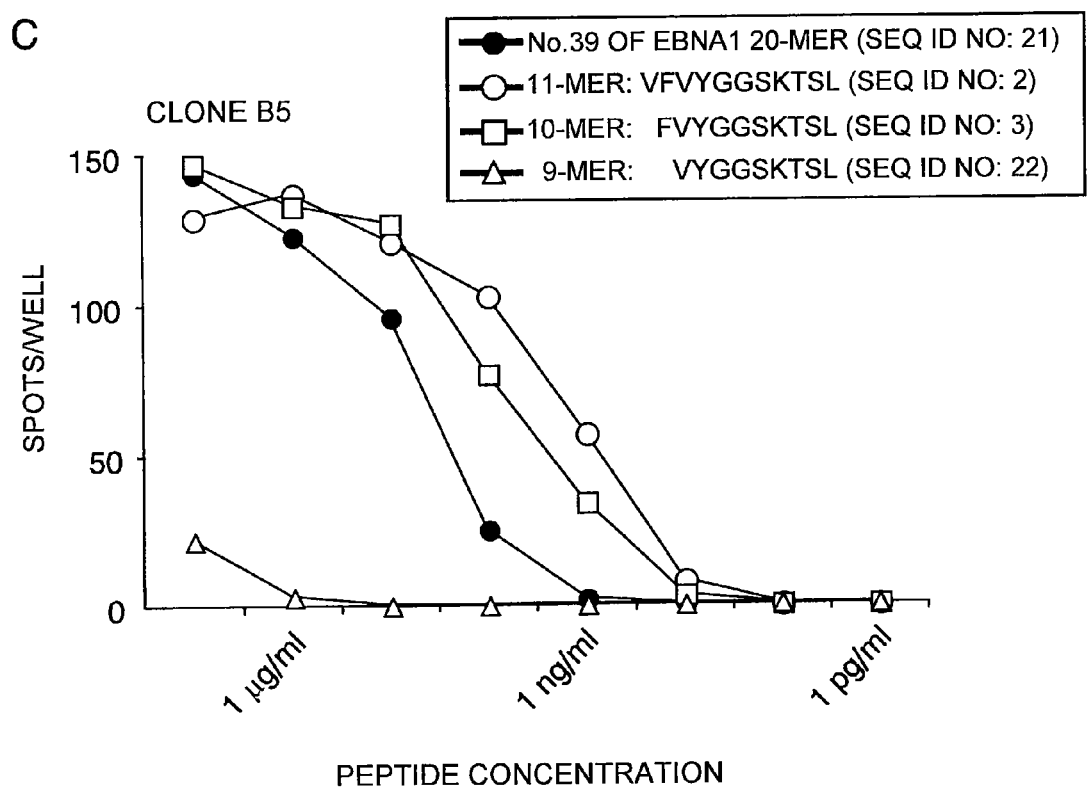

FIG. 10 (A and B) shows the identification of optimal EBNA1 antigen peptides recognized by EBNA1-specific CTL clones.

A: The amino acid sequence of the overlapping peptide recognized by the HLA-B*3501-restricted clone C6. The known epitope HPVGEADYFEY (SEQ ID NO: 28) is indicated bold and underlined. The numerals under the sequences show the numbers of the amino acids in the EBNA1 protein.

B: The amino acid sequences of two consecutive, overlapping peptides recognized by clone B5 and the optimal epitope sequences. The overlapping sequence between #38 and #39 peptides is indicated underlined. Arrows indicate the primary and auxiliary anchors for fixing HLA-Cw*0303 predicted by the program SYFPEITHI. The numerals under the sequences show the numbers of the amino acid positions in the EBNA1 protein.

FIG. 10 (C) shows the titration of EBNA1-induced synthetic peptides. Autologous CD40-B cells were incubated for one hour with 10-fold serial dilutions of synthetic peptides 507-526 (#39, 20 mer), 507-517 (11 mer), 508-517 (10 mer), and 509-517 (9 mer). CTL clone B5 (200 cells/well) was subsequently added and cultured for 20 hours. Each symbol indicates the mean number of spots in duplicate wells.

Figure 11:
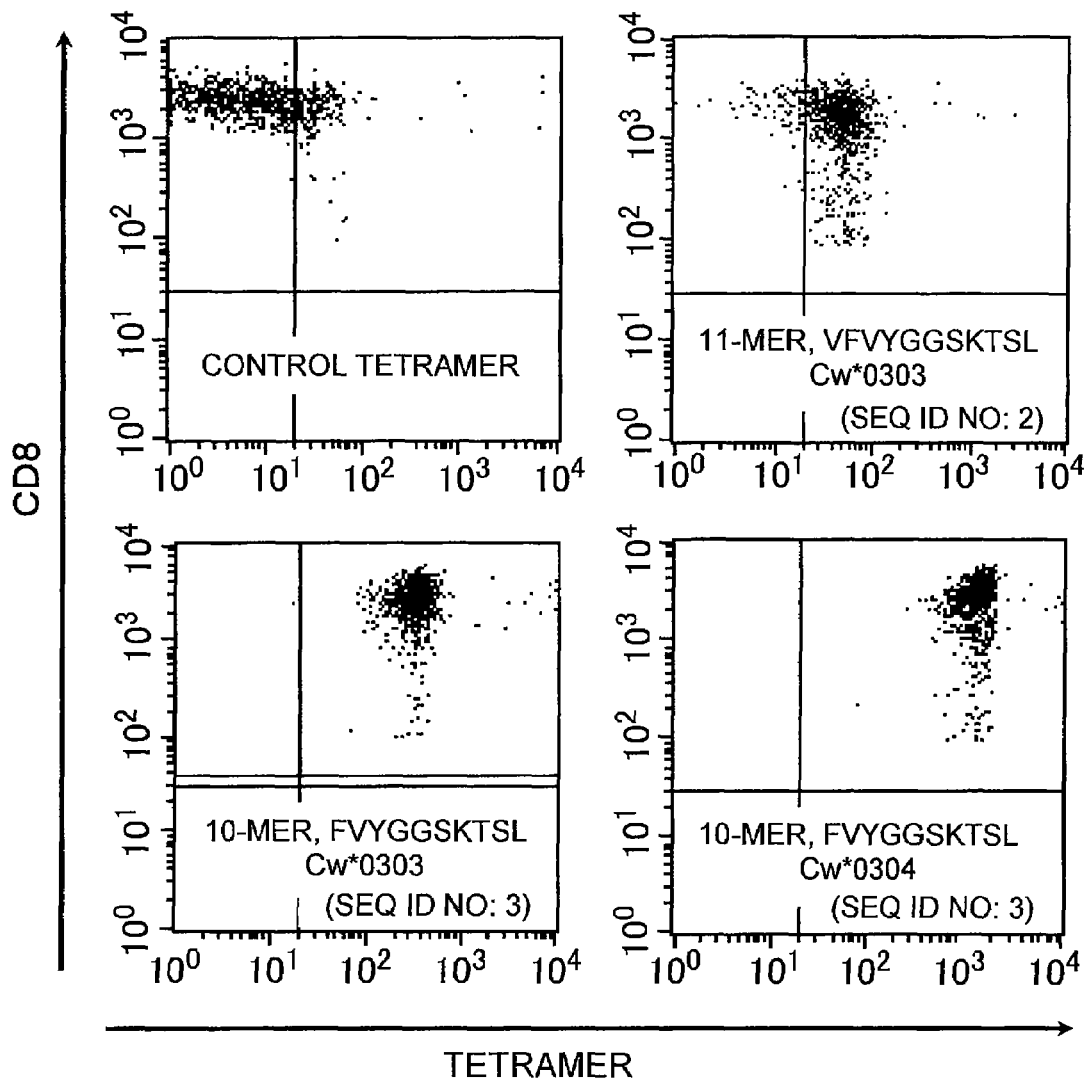

FIG. 11 shows the specific binding of HLA-Cw*0303 and HLA-Cw*0304 tetramers to B5 CTL clones. The HLA-Cw*0303-restricted EBNA1-specific CTL clone B5 was stained with PE-conjugated HLA-Cw*0303-FVYGGSKTSL (SEQ ID NO: 3), HLA-Cw*0303-VFVYGGSKTSL (SEQ ID NO: 2), or HLA-Cw*0304-FVYGGSKTSL (SEQ ID NO: 3) tetramer complexes and FITC-labeled anti-CD8 antibodies, and analyzed by flow cytometry.

Figure 12:
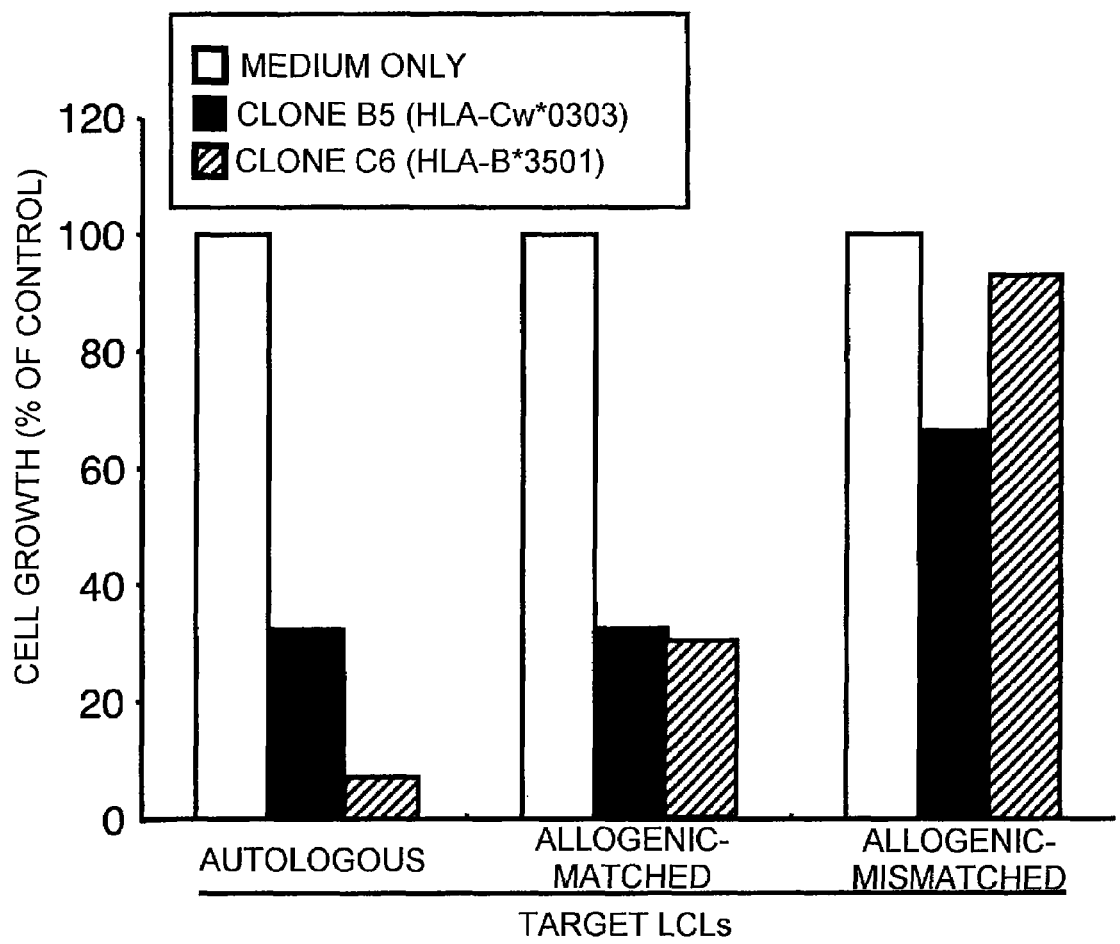

FIG. 12 shows the in vitro inhibition of HLA-matched LCL outgrowth by EBNA1-specific CTL clones. Target LCLs (2×10⁴) were cultured in triplicates in round-bottom 96-well plates with EBNA1-specific CTL clones (1×10⁴) or medium alone (negative control) and assessed for cell growth after four weeks. The outgrowing cells were verified to be LCLs by CD19 expression. Data from one representative experiment out of two are shown.

BEST MODE FOR CARRYING OUT THE INVENTION

The present invention relates to T cell epitope peptides having a function capable of inducing EBV-specific CTLs. Thus, the present invention provides EBV-specific CTL epitope peptides. Herein, the epitope peptides are referred to as "epitope peptides" or simply "peptides of the present invention".

The "peptides" of the present invention refer to biologically active linear chains of amino acid molecules that are linked together via peptide bonds between α-amino and carboxyl groups of adjacent amino acid residues. The "peptides" of the present invention are not restricted to those with a specific length and thus may be varied in length. Thus, the peptides of the present invention also include so-called "oligopeptides" and "polypeptides".

Furthermore, such a peptide may be uncharged or in its salt form, while in some cases it can be modified by glycosylation, amidation, phosphorylation, carboxylation, phosphorylation, etc.

An example of a method for selecting candidate epitope peptides is described below.

1. Computer Analysis

Candidates for EBV-specific CTL epitope peptides of the present invention can be selected through searches using multiple softwares disclosed on the Internet (Pingping G., et al., Nucleic Acids Res., 31:3621-3624 (2003)) which can be used to search epitope peptides consisting of 8 to 11 amino acids and containing each binding motif of a desired HLA molecule in the amino acid sequences of EBV proteins. The EBV proteins include EBNA1, EBNA2, EBNA3A, EBNA3B, EBNA3C, LMP1, LMP2, and leader protein in the present invention, and more preferably are EBNA1 or LMP1. The amino acid sequence and oligonucleotide sequence of EBNA1 are shown as SEQ ID NOs: 36 and 37, respectively. The amino acid sequence and oligonucleotide sequence of LMP1 with an N-terminal defect are shown as SEQ ID NOs: 34 and 35, respectively.

2. Evaluation Using Anchor Motifs

HLA-class I molecules are primarily HLA-A, HLA-B, and HLA-C. Epitope peptides that are presented by binding with them are composed of 8 to 11 amino acids. Amino acids at the second and ninth or tenth positions from the N terminus of an epitope peptide are most critical to binding with HLA molecules, and are thus referred to as anchor motifs. Anchor motifs have been reported to vary depending on the type of HLA molecule. For example, the peptide best known to bind to the HLA-A2 molecule, is a peptide composed of 9 or 10 amino acid residues in which Leu is arranged at the second position and Leu or Val is arranged at the ninth or tenth position from the N terminus (Sudo T., et al., J. Immunol., 155:4749-4756 (1995)). Alternatively, the peptide best known to bind to HLA-A24, which frequently arises in Asian populations, including Japanese, is a peptide composed of 9 or 10 amino acids in which Tyr, Phe, Met, or Trp is arranged at the second position and Leu, Ile, Trp, or Phe is arranged at the ninth or tenth position from the N terminus (Kondo A., et al., J. Immunol., 155:4307-4312 (1995)). Candidates of CTL epitope peptides can be selected by searching the amino acid sequences of proteins for sequences containing such anchor motifs.

3. Preparation of a Peptide Library

A library of peptides composed of about 20 amino acids in length is synthesized to cover all EBV proteins. The library is prepared such that peptides of about 20 amino acids overlap with adjacent peptide sequences by about ten amino acids (for example, 7, 8, 9, 10, 11, 12, or 13 amino acids). This enables a thorough search of all the proteins.

Not all candidate epitope peptides selected by the method described above can serve as CTL epitopes. They can be used as EBV-specific CTL epitopes only after the studies described below. Methods for identifying the epitope peptides are described below, but are not limited thereto.

(1) Determination of Epitope Peptide—Method 1

Peripheral blood mononuclear cells (PBMCs) isolated from a person with a history of EBV infection or T cells isolated from PBMCs are suspended at a cell density of 0.1 to $2 \times 10^6$ cells/mL in an adequate culture medium. Isolated and cultured EBV-infected cells derived from the same person are then added at $1 \times 10^5$ cells/mL to the suspension. The cells are cultured in a 5% carbon dioxide gas ($CO_2$) incubator at 37° C. for seven days. After seven days of culture, EBV-infected cells and interleukin 2 (IL-2) are added to the suspension. Then, the stimulation with EBV-infected cells and IL-2 is repeated every week to induce CTLs. Whether CTLs induced by the above procedure have a specificity to candidate epitope peptides can be assessed using the MHC-tetramer method, ELISPOT assay, chromium release assay, intracellular cytokine staining, or such (Current Protocols in Immunology, Edited by: John E. Coligan, Ada M. Kruisbeek, David H. Margulies, Ethan M. Shevach, Warren Strober, 6.19 ELISPOT Assay to Detect Cytokine-Secreting Murine and Human Cells, 6.24 Detection of Intracellular Cytokines by Flow Cytometry, published by John Wiley & Sons, Inc.).

(2) Determination of Epitope Peptide—Method 2

PBMCs isolated from a person with a history of EBV infection are suspended at a cell density of 0.1 to $2 \times 10^6$ cells/mL in an adequate culture medium, and an arbitrary candidate epitope peptide is added thereto at a concentration of 0.01 to 100 µg/mL. After two days of culture in a 5% $CO_2$ incubator at 37° C., IL-2 is added. Then, the stimulation with the above peptide and IL-2 is repeated every week or every two weeks to induce CTLs. Whether CTLs induced by the above procedure have a specificity to candidate epitope peptides can be assessed using the MHC-tetramer method, ELISPOT assay, chromium release assay, intracellular cytokine staining, or such.

(3) Determination of Epitope Peptide—Method 3

PBMCs isolated from a person with EBV infection are suspended at a cell density of 0.1 to $2 \times 10^6$ cells/mL in an adequate culture medium, and libraries of synthesized peptides pooled into an appropriate number (for example, ten types of peptides) is added thereto. After two days of culture in a 5% $CO_2$ incubator at 37° C., IL-2 is added. Then, the stimulation with the pooled peptide and IL-2 is repeated every week or every two weeks to induce CTLs. Whether CTLs induced by the above procedure have a specificity to candidate epitope peptides can be assayed using the ELISPOT assay, chromium release assay, intracellular cytokine staining, or such. When a pooled peptide gives a favorable result, a peptide(s) having the ability to induce CTLs can be selected by repeating the above-described experiment using each single peptide. The reacted peptide is shortened successively to obtain a key peptide as an epitope peptide of the present invention. In general, epitope peptides can be finally shortened to 8 to 11 amino acids.

Specifically, the peptides of the present invention include, for example, peptides comprising the nucleotide sequence of any one of SEQ ID NOs: 1 to 3.

Alternatively, the peptides of the present invention may be peptides comprising any one of the amino acid regions of SEQ ID NOs: 1 to 3. In a preferred embodiment, the peptides of the present invention are peptides in which the EBV-specific CTL epitope peptides comprise at least one amino acid sequence selected from the group consisting of the amino acid sequences of SEQ ID NOs: 1 to 3.

Furthermore, the epitope peptides of the present invention may be modified products of the above peptides, so long as their biological and immunological activities are not substantially altered and no adverse activity arises when administered.

In a preferred embodiment, the peptides of the present invention include peptides comprising an amino acid sequence with a substitution, deletion, insertion, and/or addition of one or more amino acids in any one of the amino acid sequences of SEQ ID NOs: 1 to 3, which have a function equivalent to the peptide of any one of SEQ ID NOs: 1 to 3 before the modification.

The above-mentioned "equivalent function" includes, for example, (1) the function of being able to induce EBV-specific CTLs; or (2) the function of being able to induce CTLs that have a T cell receptor capable of specifically recognizing cells presenting a complex with human major histocompatibility antigen, in particular HLA-A*0206, HLA-Cw*0303 or HLA-Cw*0304 molecule, or the like, on the cell surface.

Whether a modified peptide has a function described above can be evaluated, for example, using the methods described in the Examples herein below, or using the methods with appropriate modifications.

The peptides of the present invention include those that have been modified from their naturally existing states, or those that remain unmodified. Modifications include acetylation, acylation, ADP-ribosylation, amidation, covalent attachment of flavin, covalent attachment of heme moiety/ moieties, covalent attachment of nucleotides or nucleotide derivatives, covalent attachment of lipids or lipid derivatives, covalent attachment of phosphatidylinositol, cross-linking, cyclization, formation of disulfide bonds, methylation, demethylation, formation of covalent cross-links, formation of cystine, formation of pyroglutamate, formylation, γ-carboxylation, glycosylation, formation of GPI anchors, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Furthermore, the peptides of the present invention may comprise additional amino acid sequences attached to their N or C terminus. In addition, the peptides of the present invention can also be used in the form of a polymer, a complex with a saccharide, polyethylene glycol, lipid, and such, or a derivative with a radioisotope and such. Alternatively, in the present invention, amino acids include so-called "amino acid analogs". Such amino acid analogs include, for example, N-acylation, O-acylation, esterification, acidamidation, and alkylation products of various amino acids.

Furthermore, a formyl group, acetyl group, t-butoxycarbonyl (t-Boc) group, or such may be linked to the N terminus or the free amino group of a peptide of the present invention and a methyl group, ethyl group, t-butyl group, benzyl group, or such may be linked to the C terminus or the free carboxyl group of a peptide of the present invention, so long as the complex of a molecule, such as HLA, and a peptide of the present invention can be recognized by CTLs that have a TCR capable of specifically recognizing cells presenting the complex on the cell surface.

Furthermore, the peptides of the present invention may be variously modified to facilitate their introduction into the body. A well-known example of such a modification that facilitates introduction into the body is the introduction of a protein transduction (PT) domain. The PT domain of human immunodeficiency virus (HIV) is a peptide constituted by the amino acids extending from position 49 to 57 (Arg Lys Lys Arg Arg Gln Arg Arg Arg/SEQ ID NO: 26) of the Tat protein. It has been reported that a protein or peptide sequence of interest can be readily introduced into cells by adding the peptide sequence to the protein or peptide sequence before and/or after it (Ryu J., Mol. Cells., 16:385-391 (2003); and Kim D. T., J. Immunol., 159:1666-1668 (1997)).

Most antigens that are presented via an MHC class I molecule are degraded by intracellular proteasomes. Then, the degraded antigens are transferred to TAP (transporter in antigen processing), bind to the complex of MHC class I molecule and β2-microglobulin, which is associated with TAP within rough endoplasmic reticula, and are transported to the cell surface by exocytosis via Golgi apparatuses. Antigen presentation is reported to be effectively achieved when a peptide or protein of interest is fused with HSP (heart shock protein) 70, HSP90, or gp96, which are chaperons acting in the series of antigen-presenting pathway described above (Basu S., Immunity, 14:303-313 (2001)). Thus, in one embodiment, the present invention includes proteins arising from the fusion of a peptide of the present invention with the PT domain or a chaperon described above.

Furthermore, the peptides of the present invention can be prepared by various conventional peptide synthesis methods. For example, it is possible to prepare the peptides of the present invention by organic-chemical synthesis methods, such as solid-phase peptide synthesis, or by recombinant DNA techniques by preparing nucleic acids that encode the peptides. The peptides can also be synthesized using a commercially available chemical synthesizer (for example, a peptide synthesizer from Applied Biosystems).

Peptides of the present invention can further be produced by general chemical synthesis methods, according to their amino acid sequences. The methods include peptide synthesis by general liquid phase techniques and solid phase techniques. More specifically, such peptide synthesis methods include stepwise elongation methods, in which respective amino acids are sequentially synthesized one by one according to the amino acid sequence information, to thereby elongate the chain, and fragment condensation methods, in which fragments composed of several amino acids are prepared by prior synthesis, and then the respective fragments are coupled. Either of these methods may be employed to synthesize peptides of the present invention.

Condensation methods employed in the peptide synthesis methods may be performed in accordance with various methods. Specific examples include the azide method, the mixed acid anhydride method, the DCC method, the active ester method, the oxidation-reduction method, the DPPA (diphenylphosphorylazide) method, and the Woodward method.

Solvents generally used in these various methods can be suitably employed. Examples thereof include dimethylformamide (DMF), dimethylsulfoxide (DMSO), hexaphosphoramide, dioxane, tetrahydrofuran (THF), ethyl acetate, and mixtures thereof. In the peptide synthesis reactions described above, a carboxyl group contained in an amino acid or in a peptide that is not involved in the reaction may typically be protected through esterification to form, for example, lower-alkyl esters such as a methyl ester, an ethyl ester, or a tert-butyl ester; a benzyl ester; a p-methoxybenzyl ester; a p-nitrobenzyl ester; or an aralkyl ester. Moreover, amino acids that have a functional group in their side chains, for example, the hydroxyl group of Tyr, may be protected with an acetyl group, a benzyl group, a benzyloxycarbonyl group, or a tert-butyl group. Such protection is not necessarily essential, however. For example, the guanidino group of Arg may be protected with an appropriate protecting group such as a nitro group, a tosyl group, a 2-methoxybenzenesulfonyl group, a methicillen-2-sulfonyl group, a benzyloxycarbonyl group, an isobornyloxycarbonyl group, or an adamantyloxycarbonyl group.

The peptides of the present invention that can be obtained as described above may be suitably purified through conventional methods, such as methods that are routinely used in the field of peptide chemistry, including ion exchange resin methods, partition chromatography, gel chromatography, affinity chromatography, high performance liquid chromatography (HPLC), and countercurrent distribution approaches.

Peptides of the present invention can also be obtained through genetic engineering techniques in which a DNA nucleic acid molecule encoding a peptide of the present invention is synthesized, and then introduced into an appropriate expression vector, and expressed in a host cell.

As an example, first, nucleic acids encoding any one of the amino acid sequence of SEQ ID NOs: 1 to 3 are synthesized. Examples of suitable methods include chemical synthesis methods such as a phosphotriester method, a phosphoamidite method (Letsinger R. L., et al., J. Am. Chem. Soc., 89:4801 (1967); Letsinger R. L., et al., J. Am. Chem. Soc., 91:3350-3355 (1969); Merrifield R. B., et al., Science, 150:178-185 (1968); Beaucage S. L. and Caruthers M. H., Tetrahedron Lett., 22:1859-1862 (1981); and McBride L. J. and Caruthers M. H., Tetrahedron Lett., 24:245 (1983)), and combinations of such methods. More specifically, the DNA can also be chemically synthesized through a phosphoramidite method or a triester method, and one may use a commercially available automated device for polynucleotide synthesis. A double-stranded fragment can also be obtained from chemically synthesized single-stranded products, by synthesizing complementary strands and then by annealing the strands under appropriate conditions, or by using an appropriate primer sequence together with a DNA polymerase to add the complementary strand.

As described above, peptides of the present invention include peptides functionally equivalent to the epitope peptides (SEQ ID NOs: 1 to 3) identified herein.

To prepare a peptide functionally equivalent to another peptide, for example, methods for introducing mutations into amino acids of peptides are well known to those skilled in the art. Specifically, those skilled in the art can prepare a peptide functionally equivalent to peptides comprising any one of the amino acid sequence of SEQ ID NOs: 1 to 3 by introducing appropriate mutations into the original sequence using site-directed mutagenesis (Hashimoto-Gotoh T., et al., Gene, 152: 271-275 (1995); Zoller M. J. and Smith M., Methods Enzymol., 100:468-500 (1983); Kramer W. et al., Nucleic Acids Res., 12:9441-9456 (1984); Kramer W. and Fritz H. J., Methods Enzymol., 154:350-367 (1987); Kunkel T. A., Proc. Natl. Acad. Sci. USA, 82:488-492 (1985); and Kunkel T. A., Methods Enzymol., 85:2763-2766 (1988)). Amino acid mutations in peptides may also occur in nature. Thus, both artificially synthesized and naturally occurring proteins comprising an amino acid sequence in which one or more amino acid sequence in the sequence of the epitope peptides (SEQ ID NOs: 1 to 3) identified herein are mutated, and which is functionally equivalent to the epitope peptides, are also included in the present invention.

Examples of the objectives of the above-described amino acid modification (alteration) include modifications for:
1. increasing affinity with HLA (Rosenberg S. A., et al., Nat. Med., 4:321-327 (1998); and Berzofsky J. A., et al., Nat. Rev. Immunol., 1:209-219 (2001));
2. improving TCR recognition (Fong L., et al., Proc. Natl. Acad. Sci. USA, 98:8809-8814 (2001); and Rivoltini L., et al., Cancer Res., 59:301-306 (1999)); and
3. avoiding metabolism by peptidases and such in serum (Berzofsky J. A., et al., Nat. Rev. Immunol., 1:209-219 (2001); Parmiani G., et al., J. Natl. Cancer Inst., 94:805-818 (2002); and Brinckerhoff L. H., et al., Int. J. Cancer, 83:326-334 (1999)).

In the mutants described above, the number of mutated (substituted, inserted, deleted, and such) amino acids is not limited, so long as the function of the peptides of the present invention is retained, and the number is typically 5 or less, preferably 4 or less, more preferably 3 or less, and even more preferably 1 to 2 amino acids. Furthermore, when the above alteration involves, for example, an addition of amino acid residues to the terminus of a peptide of any one of SEQ ID NO: 1 to 3, the number of added amino acids is not limited so long as the function of the peptides of the present invention is retained, and the number is usually 20 or less, preferably 10 or less, and more preferably 5 or less, even more preferably 3 or less, and most preferably, 1 to 2 amino acids.

In mutating an amino acid, it is preferable to change it into another amino acid (amino acid similar to the unmodified amino acid) that allows the properties of the unmodified amino acid to be conserved. Examples of amino acid side chain characteristics include: side chains having hydrophobic amino acids residues (A, I, L, M, F, P, W, Y, V), hydrophilic residues (R, D, N, C, E, Q, G, H, K, S, T), residues with an aliphatic side chain (G, A, V, L, I, P), residues with a side chain containing a hydroxyl group (S, T, Y), residues with a side chain containing sulfur (C, M), residues with a side chain containing a carboxylic acid and amide group (D, N, E, Q), basic residues (R, K, H), and aromatic residues (H, F, Y, W) (amino acids are shown using the standard one-letter code in the parentheses).

Peptides having a modified amino acid sequence, in which one or more amino acids are deleted, added, and/or substituted with another amino acid, are known to maintain the original biological function (activity) (Mark D. F., et al., Proc. Natl. Acad. Sci. USA, 81:5662-5666 (1984); Zoller M. J. and Smith M., Nucleic Acids Res., 10:6487-6500 (1982); Wang A., et al., Science 224:1431-1433 (1984); and Dalbadie-Mc-Farland G., et al., Proc. Natl. Acad. Sci. USA, 79:6409-6413 (1982)).

Peptides in which multiple amino acid residues are added to the amino acid sequence of a peptide of the present invention include fusion peptides comprising such a peptide. Such fusion peptides arise from fusion between the peptides of the present invention and other peptides. To produce a fusion protein, a polynucleotide encoding a peptide of the present invention (for example, the peptides of SEQ ID NOs: 1 to 3) and a polynucleotide encoding another peptide are ligated so that their frames match, and inserted into an expression vector to express in a host. Methods known to those skilled in the art can be used.

Other peptides that can be used as peptides that are fused to the peptides of the present invention can be suitably selected according to various objectives, including, for example, for isolating and purifying the peptide or for applied research, in addition to the objective of inducing CTL. Known peptides that can be used as peptides that are fused to the peptides of the present invention include, for example, FLAG (Hopp T. P., et al., Biotechnology, 6:1204-1210 (1988)), 6×His containing six histidine (His) residues, 10× His, influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to peptides of the present invention include GST (glutathione-S-transferase), HA (influenza agglutinin), immunoglobulin constant region, β-galactosidase, MBP (maltose-binding protein), and such. Fusion peptides can be prepared by fusing commercially available polynucleotides, encoding the fusion peptides or peptides discussed above, with polynucleotides encoding the peptides of the present invention, and expressing the prepared fused polynucleotides.

When a fusion comprising a peptide of the present invention is prepared, a peptide sequence which is a protease cleavage site, such as Factor Xa, enterokinase, or thrombin, may be inserted at the junction of fusion. In this case, the peptide is expressed as a peptide fusion in which a purification tag, such as GST, MBP, or FLAG tag described above, is added. After purification, regions other than the desired peptide of the present invention can be cleaved and removed from the peptide fusion by a corresponding protease, such as Factor Xa, enterokinase, or thrombin, if required. Such a treatment is useful.

Other methods for preparing peptides functionally equivalent to a certain peptide which are well known to those skilled in the art include methods using hybridization techniques (Sambrook J., et al., Molecular Cloning 2nd ed., 9.47-9.58, Cold Spring Harbor Lab. press, 1989). Generally, those skilled in the art can isolate polynucleotides highly homologous to polynucleotides encoding the peptides of the present invention based on the polynucleotides or portions thereof from samples of polynucleotides derived from various organisms (for example, derived from EBV), artificially synthesized peptide libraries, or others, and isolate peptides which are functionally equivalent to the peptides of the present invention using the polynucleotides.

The present invention includes peptides encoded by a polynucleotide that hybridizes to a polynucleotide encoding a peptide of the present invention shown in SEQ ID NOs: 1 to 3, and which is functionally equivalent to the peptide of any one of SEQ ID NOs: 1 to 3.

The conditions for hybridization used for isolating a polynucleotide encoding a peptide functionally equivalent to the peptide of SEQ ID NOs: 1 to 3 can be appropriately selected by those skilled in the art. For example, low stringency conditions may be used for hybridization. Low stringency conditions are post-hybridization washing in 0.1×SSC, 0.1% SDS at 42° C., for example, and preferably in 0.1×SSC, 0.1% SDS at 50° C. Highly stringent conditions are more preferable, which are washing in 5×SSC, 0.1% SDS at 65° C., for example. Under these conditions, a DNA having a higher homology can be efficiently obtained by increasing the temperature. Multiple factors including the temperature, salt concentration, and such are considered to affect the stringency of hybridization; one skilled in the art can achieve similar stringencies by appropriately selecting these factors.

Furthermore, by using a gene amplification technique (PCR)(Current Protocols in Molecular Biology; editor Ausubel et al.; John Wiley & Sons, Sections 6.1-6.4, 1987) in place of hybridization, polynucleotide fragments that are highly homologous to a polynucleotide encoding the peptides of the present invention (SEQ ID NOs: 1 to 3) can be isolated using primers, the design of which is based on portions of the polynucleotide encoding the peptide identified by the present inventors, to obtain a peptide that is functionally equivalent to the peptide identified by the present inventors based on the polynucleotide.

Normally, a peptide encoded by a polynucleotide isolated using the above hybridization techniques or by gene amplification, and which is functionally equivalent to the peptides of SEQ ID NOs: 1 to 3, will have a high homology with the peptides at the amino acid level. The peptides of this invention include peptides functionally equivalent to the peptides of SEQ ID NOs: 1 to 3, and having high homologies with the peptides at the amino acid level. High homology normally means an identity of at least 50% or more at the amino acid level, preferably 75% or more, more preferably 85% or more, and most preferably 95% or more (for example, 96% or more, 97% or more, 98% or more, and 99% or more). Homology between peptides can be determined according to an algorithm described in literature (Wilbur W. J. and Lipman D., J. Proc. Natl. Acad. Sci. USA, 80:726-730 (1983)).

The identity of amino acid sequences can be determined, for example, using the BLAST algorithm of Karlin and Altschul (Proc. Natl. Acad. Sci. USA, 87:2264-2268 (1990); and Proc. Natl. Acad. Sci. USA, 90:5873-5877 (1993)). Based on this algorithm, a program called BLASTX has been developed (Altschul et al., J. Mol. Biol., 215:403-410 (1990)). When amino acid sequences are analyzed using BLASTX, parameters are set, for example as follows: score=50 and wordlength=3. When BLAST and Gapped BLAST programs are used, default parameters of each program may be used. The specific procedures of these analytical methods are known (on the world wide web at ncbi.nlm.nih.gov).

The peptides of the present invention can be prepared as recombinant peptides or natural peptides using methods well known to those skilled in the art. A recombinant peptide can be prepared, for example, by inserting a polynucleotide that encodes a peptide of the present invention into an appropriate expression vector; introducing the vector into an appropriate host cell; collecting the recombinant thus obtained; obtaining an extract thereof; and purifying the peptide by subjecting the extract to a chromatographic procedure. Examples of chromatographic procedures are ion exchange chromatography, reverse phase chromatography, gel filtration, or affinity chromatography utilizing a column to which antibodies against peptides of the present invention are immobilized, or combinations of more than one of the aforementioned columns.

When the peptides are expressed within host cells (for example, animal cells or *Escherichia coli* (*E. coli*)) as recombinant peptides fused with a tag for purification (for example, histidine tag), the expressed fusion peptides can be purified using a commercially available purification column corresponding to the fused tag (nickel column when histidine tag is used).

A natural peptide can be isolated by methods well known to those skilled in the art, for example, through purification by applying extracts of tissues or cells expressing the peptide of the present invention onto an affinity column in which an antibody that binds to the peptide has been attached. The antibody may be a polyclonal or monoclonal antibody.

The above-described nucleic acids and vectors encoding a peptide of the present invention are also included in the present invention.

The nucleic acids (polynucleotides) of the present invention may be in any form, so long as they can encode a peptide of the present invention. Specifically, cDNAs synthesized from mRNAs, genomic DNAs, and chemically-synthesized DNAs can be used. In addition, polynucleotides having any nucleotide sequence based on the degeneracy of genetic code are included as long as they can encode a peptide of the present invention.

The nucleic acids (polynucleotides) of the present invention can be obtained by methods known to those skilled in the art. The nucleic acids can be appropriately produced, for example, using commercially available nucleic acid synthesizers. The nucleotide sequences of prepared polynucleotides can be determined by known methods, for example, the dideoxy nucleotide chain termination method.

Nucleic acids encoding a peptide of the present invention are important, for example, to produce the peptide of the present invention in hosts using genetic recombination techniques. In this case, it is preferred that amino acid codons are modified so that they agree with the codon usage in the host in which the peptide is to be produced, because the frequency of amino acid codon usage varies between hosts. Nucleic acids encoding a peptide of the present invention can be used as vaccines, and can be delivered as naked nucleic acids or using appropriate viral or bacterial vectors (Berzofsky J.A., et al., J. Clin. Invest., 114:450-462 (2004); Berzofsky J. A., et al., J. Clin. Invest., 113:1515-1525 (2004)). Such appropriate bacterial vectors include bacterial vectors of *Salmonella* subspecies. Appropriate viral vectors include, for example, retroviral vectors, adenoviral vectors, Sendai virus vectors, lentiviral vectors, and vaccinia vectors. An example of an appropriate vaccinia vector is modified vaccinia Ankara vectors.

In a preferred embodiment, the nucleic acids of the present invention include, for example, vectors capable of expressing the peptides of the present invention. In general, the vectors carry a DNA construct having a structure in which a nucleic acid of the present invention is operatively linked downstream of a promoter. Vectors commonly used include plasmids, viral vectors, and the like.

Those skilled in the art are capable of appropriately producing such a vector carrying the desired DNA, using common genetic engineering techniques. Normally, various commercially available expression vectors can be used.

The vectors of the present invention are also useful for retaining a polynucleotide of the present invention in a host cell or for expressing the peptides of the present invention in the host cell. A nucleic acid (polynucleotide) of the present invention is normally retained (inserted) in an appropriate vector before being introduced into a host cell. The vectors are not particularly limited, so long as they can stably retain the inserted DNA. For instance, when E. coli is used as the host, vectors such as pBluescript (Stratagene), and the like are preferred cloning vectors, although a variety of commercially available vectors may be used. If a vector is used for the purpose of producing peptides of the present invention, expression vectors are especially useful. The expression vectors are not particularly limited so long as they express the peptide in vitro, in E. coli, in culture cells, or in vivo. Examples thereof include pBEST vector (Promega) for in vitro expression, pET vector (Invitrogen) for expression in E. coli, pME18S-FL3 vector (GenBank Accession No. AB009864) for expression in cultured cells, and pME18S vector (Mol. Cell. Biol., 8:466-472 (1988)) for in vivo expression. Insertion of nucleic acids of the present invention into a vector can be performed by routine procedures, such as ligase reactions using restriction enzyme sites.

There is no particular limitation on the host cell, and various host cells may be used according to the desired purpose. Examples of cells that express peptides include bacterial cells (such as those of Streptococcus, Staphylococcus, E. coli, Streptomyces, and Bacillus subtilis), insect cells (such as Drosophila S2 and Spodoptera SF9), animal cells (such as CHO, COS, HeLa, C127, 3T3, BHK, HEK293, and Bowes melanoma cells), and plant cells. Vectors can be introduced into a host cell by well known methods, including, for example, the calcium phosphate precipitation method, the electroporation method (Current Protocols in Molecular Biology; editor: Ausubel et al., 1987; Publisher: John Wiley & Sons. Section 9.1-9.9), the lipofection method (GIBCO-BRL), and the microinjection method.

Appropriate secretion signals may be incorporated into the peptide of interest such that the peptide that has been expressed in the host cell is secreted into the lumen of the endoplasmic reticulum, into the periplasmic space, or into the extracellular environment. These signals may be endogenous to the peptide of interest or may be heterologous signals.

In the above production methods, the collection of peptides is conducted as follows: if the peptide of the present invention is secreted into the medium, the medium is collected; if the peptide of the present invention is produced within cells, the cells are first lysed before the peptide is collected.

The peptides of the present invention can be collected and purified from recombinant cell cultures by well-known methods, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography.

Moreover, methods for expressing the polynucleotides (nucleic acid) of the present invention in the living body of an animal include methods in which the nucleic acid of the present invention is incorporated into an appropriate vector and the vector is introduced into the living body by the retrovirus method, the liposome method, the cationic liposome method, the EBV method, or the like. In this way, immunotherapy can be performed. Examples of the vectors to be used include retroviral vectors, but are not limited thereto. General gene manipulations such as the insertion of the DNA of the present invention into a vector can be performed in accordance with routine methods (Molecular Cloning, 5.61-5.63).

The administration into the living body can be performed either by the ex vivo method or the in vivo method.

The peptides of the present invention (EBV-specific CTL epitope peptides) can be used as peptide vaccines in active immunotherapy. More specifically, vaccines comprising CTL epitope peptides of the present invention can be administered to a healthy individual or to a patient, made to proliferate (the EBV-specific CTLs) within the body, and used to prevent or treat diseases. Depending on the purpose of vaccination, an epitope peptide can be used alone or two or more different types of peptides can be mixed and used in combination.

Thus, the present invention provides vaccines for treating or preventing EBV infection or cancers positive for the virus, which include, as an active ingredient, peptides or nucleic acids of the present invention.

The "vaccines" of the present invention can also be referred to as "active immunotherapeutic agents", "immunotherapeutic agents", or "therapeutic agents for EBV-associated diseases". Alternatively, herein, the "therapeutic agents" can also be referred to as "pharmaceuticals", "pharmaceutical compositions", "therapeutic medicines", or the like.

Furthermore, antigen-presenting cells that present CTL epitope peptides of the present invention can be used as vaccines in active immunotherapy. The "antigen-presenting cells that present CTL epitope peptides" refers to:
1. epitope peptide-pulsed antigen-presenting cells, which are prepared by mixing antigen-presenting cells with a CTL epitope peptide in an adequate culture medium for 30 minutes to one hour;
2. antigen-presenting cells made to present a CTL epitope peptide by gene transfer and such using a nucleic acid encoding the CTL epitope peptide;
3. artificially produced antigen-presenting cells having the ability to present an antigen; and such.

The antigen-presenting cells refer, for example, to dendritic cells, B cells, macrophages, and certain types of T cells, which express HLA capable of binding with the peptides on their surface and have the ability to stimulate CTLs. Artificially produced antigen-presenting cells having the ability to present an antigen can be prepared, for example, by immobilizing the ternary complex of HLA, CTL epitope peptide, and β2-microglobulin onto a lipid bilayer, plastic or latex beads, or such, and immobilizing either a costimulatory molecule such as CD80, CD83, or CD86 that can stimulate CTLs, or an antibody or the like that acts agonistically to CD28, which is a T cell ligand that binds to costimulatory molecules (Oelke M., et al., Nat. Med., 9:619-624 (2003); Walter S., et al., J. Immunol., 171:4974-4978 (2003); Oosten L. E., et al., Blood, 104:224-226 (2004)).

Thus, in a preferred embodiment, the present invention provides vaccines including, as an active ingredient, antigen-presenting cells that present a peptide of the present invention by HLA.

The nucleic acids of the present invention can be used as DNA vaccines, recombinant viral vector vaccines, or such in active immunotherapy. In this case, it is preferred that the nucleotide sequences of CTL epitope peptides are altered to be compatible with the codon usage in the host in which the recombinant vaccines or recombinant viral vaccines are produced (Casimiro D. R., et al., J. Virol., 77:6305-6313 (2003); Berzofsky J. A., et al., J. Clin. Invest., 114:450-462 (2004)).

Vaccines including a peptide of the present invention or antigen-presenting cells that present a peptide of the present invention can be prepared by methods known in the technical field. Such vaccines include, for example, agents, such as injections and solid agents, including, as an active ingredient, a peptide of the present invention.

The peptides of the present invention can be used in producing passive immunotherapeutic agents against EBV. EBV-specific CTLs obtained by the procedure described herein below are suspended in PBS containing human albumin or the like, and used as passive immunotherapeutic agents against EBV. The EBV-specific CTLs included in the passive immunotherapeutic agents can be obtained by the preparation methods described below. CTLs can also be used after purification to improve the purity.

Specific methods for preparing CTLs are described below. However, methods for preparing CTLs are not limited to these.

(a) Preparation of CTLs—Method 1

PBMCs are reacted with an adequate concentration of an EBV-specific epitope peptide-tetramer reagent. EBV-specific CTLs bound to the epitope peptide-tetramer reagent are stained with a labeling dye. Thus, stained CTLs are isolated alone using a cell sorter, microscope, or such. The growth of the resulting isolated EBV-specific CTLs is stimulated with a T cell stimulator such as anti-CD3 antibody, PHA, or IL-2, or with antigen-presenting cells whose growth potential has been eliminated by X-ray irradiation, mitomycin treatment, or such, to obtain the required number of cells for passive immunotherapy.

(b) Preparation of CTLs—Method 2

An EBV-specific epitope peptide monomer and/or epitope peptide tetramer reagent is immobilized on a sterile plate or such, and PBMCs are cultured in the plate. To isolate EBV-specific CTLs that are bound to the epitope peptide monomer and/or epitope peptide tetramer, which is immobilized on the plate, unbound floating cells are washed off, and then only the antigen-specific CTLs remaining on the plate are suspended in a fresh culture medium. The resulting isolated EBV-specific CTLs are stimulated for growth with a T cell stimulator, such as anti-CD3 antibody, PHA, or IL-2, or with antigen-presenting cells whose growth potential has been eliminated by X-ray irradiation, mitomycin treatment, or such, to obtain the required number of cells for passive immunotherapy.

(c) Preparation of CTLs—Method 3

An EBV-specific epitope peptide monomer and/or epitope peptide tetramer reagent and a costimulatory molecule, such as CD80, CD83, or CD86, or an antibody or the like, which act agonistically to CD28, a T cell ligand that binds to the costimulatory molecule are immobilized on a sterile plate or such, and PBMCs are cultured in the plate. After two days, IL-2 is added to the culture medium. The cells are cultured in a 5% $CO_2$ incubator at 37° C. for seven to ten days. The cultured cells are collected, and then further cultured in a fresh plate on which the above molecules are immobilized. This process is repeated to obtain the required number of CTLs for passive immunotherapy.

(d) Preparation of CTLs—Method 4

PBMCs or T cells are stimulated directly with a CTL epitope peptide of the present invention, or with antigen-presenting cells pulsed with the peptide, antigen-presenting cells introduced with the gene, or artificially produced antigen-presenting cells having the ability to present antigens. CTLs induced by the stimulation are cultured in a 5% $CO_2$ incubator at 37° C. for seven to ten days. The stimulation with the CTL epitope peptide and IL-2, or with the antigen-presenting cells and IL-2 is repeated every week to obtain the required number of CTLs for passive immunotherapy.

Epitope peptide-monomers and epitope peptide-tetramers using the peptides of the present invention (EBV-specific CTL epitope peptides) can be prepared by known methods (U.S. Pat. No. 5,635,363, Inventors: J. D. Altman, M. G. McHeyzer-Williams, Mark M. Davis, Compositions and methods for the detection, quantitation and purification of antigen-specific T cells; French Application Number FR9911133, Inventor: M. Bonneville, et al., Means for detecting and for purifying $CD8^+$ T-lymphocyte populations specific for peptides presented in the HLA context). The epitope peptide-monomer, which is the complex of HLA class I molecule purified from a genetically modified host for protein expression, β2-microglobulin, and a CTL epitope peptide of the present invention, is formed in a buffer. A biotin-binding site is added to the C terminus of the recombinant HLA class I molecule beforehand. After epitope peptide-monomer formation, biotin is allowed to bind to this site. The epitope peptide-tetramer can be prepared by combining commercially available dye-labeled streptavidin with a biotinylated epitope peptide-monomer at a molar ratio of 1:4.

When the proportion of specific CTLs is low in the methods for preparing CTLs, highly pure CTLs can be collected by the methods described below, if required.

(a) Purification Using Epitope Peptide-tetramer Reagent

An EBV-specific epitope peptide-tetramer reagent is reacted with CTLs induced by the methods for preparing CTLs. The specific CTLs can be isolated using a magnetically-labeled secondary antibody against a labeling dye that labels the epitope peptide-tetramer. Such magnetically-labeled secondary antibodies and magnetic cell separation devices are available from Dynal Co. or Miltenyi Biotec GmbH. The resulting isolated EBV-specific CTLs are stimulated for growth with a T cell stimulator, such as anti-CD3 antibody, PHA, or IL-2, to obtain the required number of cells for passive immunotherapy.

(b) Purification Using Secreted Cytokines

EBV-specific CTLs can be purified by using cytokines or the like released from EBV-specific CTLs. For example, using a kit available from Miltenyi Biotec GmbH, cytokines released from CTLs are captured by specific antibodies on the cell surface. The cells are stained with cytokine-specific labeled antibodies and then with a magnetically labeled label-specific antibody. Then, the cells can be purified using a device for separating magnetically labeled cells. The growth of the resulting isolated EBV-specific CTLs is stimulated with a T cell stimulator such as anti-CD3 antibody, PHA, or IL-2, to obtain the required number of cells for passive immunotherapy.

(c) Purification Using Cell Surface Protein-specific Antibodies

It is reported that on the cell surface of specific CTLs, the expression of some cell surface proteins (for example, CD107a, CD107b, CD63, CD69, etc.) is enhanced upon stimulation with specific peptides (Betts M. R. et al., J. Immunol. Methods, 281:65-78 (2003); Trimble L. A., et al., J. Virol., 74:7320-7330 (2000)). By magnetically labeling specific antibodies against such proteins, CTLs can be purified using a magnetic separation device or such. Alternatively, CTLs can also be purified by magnetically labeling anti-IgG antibodies or such against the specific antibody. Alternatively, specific CTLs can also be purified by coating a plastic culture plate with such an antibody, culturing stimulated PBMCs in the plate, and washing off unbound cells. The resulting isolated EBV-specific CTLs are stimulated for growth with a T cell stimulator such as anti-CD3 antibody, PHA, or IL-2, to obtain the required number of cells for passive immunotherapy.

The present invention provides passive immunotherapeutic agents against EBV (immunotherapeutic agents) including, as an active ingredient, CTLs obtained and purified as described above.

The "passive immunotherapeutic agents" of the present invention can also be referred to as "immunotherapeutic agents", "therapeutic agents for EBV-associated diseases", or "CTL inducers".

In a preferred embodiment of the present invention, the passive immunotherapeutic agents are passive immunotherapeutic agents against EBV including, as an active ingredient, EBV-specific CTLs that are obtained by stimulating peripheral blood lymphocytes with the peptides of the present invention or antigen-presenting cells that present the peptides by HLA.

Another embodiment is passive immunotherapeutic agents against EBV, which include as an active ingredient, CTLs that are obtained by reacting peripheral blood lymphocytes with a major histocompatibility antigen complex and/or major histocompatibility antigen complex-tetramer prepared from the peptides of the present invention, allowing the formation of a complex in which the major histocompatibility antigen complex and/or major histocompatibility antigen complex-tetramer is bound to CTLs, and isolating the CTLs from the complex.

The agents of the present invention (the vaccines, passive immunotherapeutic agents and such of the present invention) can be combined with a physiologically acceptable carrier, excipient, diluent, or the like, and then administered orally or parenterally as pharmaceutical compositions. The dosage form for oral agents may be granules, powders, tablets, capsules, solutions, emulsions, suspensions, or the like. The dosage form for parenteral agents may be selected from injections, drops, external medicines, suppositories, or the like. Examples of injections include agents for subcutaneous injection, intramuscular injection, and intraperitoneal injection. Examples of external medicines include agents for nasal administration and ointments. Preparation methods for preparing the above dosage forms to include agents of the present invention as the main ingredients are known.

For example, tablets for oral administration can be produced by mixing the agents of the present invention with excipients, disintegrants, binders, lubricants, and the like, and by compression and shaping.

For example, antigen-presenting cells that present the peptides of the present invention can be used in combination with pharmaceutically acceptable excipients that do not affect the activity of the peptides or the cells. Examples include, water, saline, dextrose, ethanol, glycerol, dimethyl sulphoxide (DMSO), and other adjuvants or mixtures thereof. Furthermore, an auxiliary agent such as albumin, a wetting agent, or an emulsifying agent can be added if needed. Commonly used disintegrants include calcium carbonate, carboxymethylcellulose calcium, and the like. Binders include gum arabic, carboxymethylcellulose, and polyvinylpyrrolidone. Known lubricants include talc, magnesium stearate, and such.

Tablets including the agents of the present invention can be masked or coated to form enteric preparations by known methods. Ethylcellulose, polyoxyethyleneglycol, and the like may be used as coating agents.

Moreover, injectable preparations can be obtained by mixing the agents of the present invention, serving as the main ingredients, with an appropriate dispersing agent, or by dissolving or dispersing them in a dispersion medium. The agents may be in the form of either an aqueous preparation or an oil-based preparation by appropriate selection of dispersion medium. Distilled water, physiological saline, Ringer's solution, or the like is used as dispersion media when preparing aqueous preparations. Various vegetable oils, propylene glycol, or the like, is used as dispersion media for oil-based preparations. Preservatives such as paraben may also be added as required. Moreover, publicly known isotonizing agents such as sodium chloride and glucose can be added to the injectable preparations. Furthermore, soothing agents such as benzalkonium chloride and procaine hydrochloride can be added.

Moreover, external preparations can be produced by forming the agents of the present invention into solid, liquid, or semisolid compositions. In the case of solid or liquid compositions, external preparations can be produced by making compositions similar to those described above. Semisolid compositions can be prepared by adding thickeners to appropriate solvents as required. Water, ethyl alcohol, polyethylene glycol, or the like can be used as solvents. Bentonite, polyvinyl alcohol, acrylic acid, methacrylic acid, polyvinylpyrrolidone, or the like are commonly used as thickeners. Preservatives such as benzalkonium chloride can be added to these compositions. Moreover, these compositions can also be combined with oil bases such as cacao butter or with aqueous gel bases such as cellulose derivatives as carriers, to prepare suppositories.

Furthermore, the peptides of the present invention can be prescribed in neutral or salt form. Examples of pharmaceutically acceptable salts include inorganic salts such as hydrochloric acid and phosphoric acid, and organic salts such as acetic acid and tartaric acid.

If the agents of the present invention are used as agents for gene therapy, there are methods of directly administering the agents of the present invention by injection, and methods of administering vectors incorporating a nucleic acid. Examples of the vectors include adenoviral vectors, adeno-associated viral vectors, herpesvirus vectors, vaccinia virus vectors, retroviral vectors, and lentiviral vectors. The use of such viral vectors enables efficient administration of therapeutic agents.

Moreover, it is possible to introduce the agents of the present invention into phospholipid vesicles such as liposomes and then to administer the vesicles. For example, vesicles retaining the peptides or vectors of the present invention are introduced into given cells by the lipofection method. Cells thus obtained are systemically administered into a vein or an artery, or the like.

The agents of the present invention can be administrated parenterally or orally. When the chief ingredient in the agents is a peptide, in general, parenteral administration is preferred. Parenteral administration includes nasal administration, injection such as subcutaneous, intramuscular, or intravenous injection, suppository, etc. Meanwhile, for oral administration, the agents can be prepared as mixtures with excipients such as starch, mannitol, lactose, magnesium stearate, and cellulose.

The vaccines of the present invention are administered at a therapeutically effective dose. The dose depends on the subject to be treated and the immune system. Necessary doses are determined by physicians. Typically, the appropriate dose is 1 mg to 100 mg of the peptide of the present invention (epitope peptide) per patient, or $10^6$ to $10^9$ epitope peptide-pulsed cells per patient. Furthermore, the administration intervals can be set according to the subject and purpose.

Furthermore, EBV-associated diseases on which an agent of the present invention is expected to produce a preventive or therapeutic effect include, for example, malignant tumors such as Burkitt's lymphoma (BL), Hodgkin's disease (HD), nasopharyngeal cancer (NPC), and post-transplant lymphoproliferative disorder (PTLD).

Animals that can be inoculated with the agents (vaccines) of the present invention are not particularly limited, as long as they have an immune system and can be infected with EBV. The animals are preferably humans.

The present invention also provides methods for inducing (activating) CTLs, which include inducing CTLs using the peptides of the present invention.

Preferred embodiments of the induction methods of the present invention relate to methods for inducing EBV-specific CTLs by contacting peripheral blood mononuclear cells with the peptides of the present invention (for example, antigen peptides restricted by HLA-A24 or the like) in a culture medium containing plasma.

In addition, methods for detecting or quantifying EBV-specific CTLs that are induced by the methods described above are also included in the present invention.

Furthermore, EBV-specific CTLs included by the above-described methods can be used as an ingredient of passive immunotherapeutic agents against EBV. Thus, passive immunotherapeutic agents can be produced by inducing EBV-specific CTLs using the above-described methods, and obtaining the T cells.

The present invention provides methods for producing passive immunotherapeutic agents, which use the method of the present invention for inducing EBV-specific CTLs.

Preferred embodiments of the production methods are methods that include the step of obtaining EBV-specific CTLs by stimulating peripheral blood lymphocytes with the peptides of the present invention or with antigen-presenting cells that present the peptides by HLA.

In another preferred embodiment, the methods are for producing passive immunotherapeutic agents against EBV, which include the step of obtaining CTLs by reacting peripheral blood lymphocytes with the major histocompatibility antigen complex and/or major histocompatibility antigen complex-tetramer prepared from the peptides of the present invention, allowing the formation of a complex in which the major histocompatibility antigen complex and/or major histocompatibility antigen complex-tetramer are bound with CTLs, and isolating CTLs from the complex.

The production methods described above may include, in addition to the steps described above, the step of "mixing pharmaceutically acceptable carriers to the isolated CTLs", if required.

Furthermore, MHC-tetramer reagents prepared using the peptides of the present invention can be used not only to quantify specific CTLs but also to simultaneously assess the differentiation stages and functionality of specific CTLs, by combining with antibodies specific to cell surface proteins or with methods for quantifying cells producing intracellular cytokines.

Further, the present invention provides methods for quantifying (detecting or assaying) EBV-specific CTLs using the peptides of the present invention.

It is important to know whether EBV-specific CTLs are present in peripheral blood of high-risk patients (persons with reduced immunocompetence for some reason, patients with congenital immunodeficiency, patients who receive an immunosuppressant to prevent rejection after transplantation of bone marrow, hematopoietic stem cells, cord blood, or a solid organ, patients with chronic virus infection, AIDS patients, elderly people, babies and infants, pregnant women, etc.), because such information is useful for infection management, including the appropriate use of anti-viral agents and immunosuppressants. EBV-specific CTLs can be quantified, for example, by the following three methods using the peptides of the present invention (CTL epitope peptides); however, such methods are not limited to these.

(a) Quantitation Method 1

EBV-specific CTLs in peripheral blood can be quantified by using epitope peptide-tetramer reagents produced using CTL epitope peptides of the present invention. Quantitation can be carried out, for example, by the following procedure. Peripheral blood or PBMCs are reacted with an adequate concentration of an epitope peptide-tetramer reagent. When bound to the epitope peptide-tetramer reagent, CTLs are stained with a labeling dye. Thus, stained CTLs are counted using a flow cytometer, microscope, or such. The T cell subsets of EBV-specific CTLs can also be determined at the same time by reacting an anti-CD3 antibody, anti-CD4 antibody, anti-CD8 antibody, or the like, which is labeled with a dye that is different from that of the epitope peptide-tetramer reagent at the time of reaction with the epitope peptide-tetramer reagent.

(b) Quantitation Method 2

This method quantifies cytokines and/or chemokines such as interferon gamma (IFNγ), tumor necrosis factor (TNF), or interleukin, produced by CTLs upon stimulation of PBMCs with the CTL epitope peptides of the present invention. This method is illustrated below in more detail by using IFNγ as an example parameter.

b-1. Method Based on Cytokine Quantitation 1 (Quantitation of Cells Producing Intracellular IFNγ)

PBMCs are suspended at a cell density of about $2 \times 10^6$ cells/mL in an adequate culture medium, and CTL epitope peptides of the present invention are added thereto. Furthermore, an agent that inhibits intracellular protein transport (for example, brefeldin A, monensin, or such) is added, and the cells are cultured in a 5% $CO_2$ incubator at 37° C. for 5 to 16 hours. After culture, the cells are reacted with an antibody against a T cell marker (anti-CD3 antibody, anti-CD4 antibody, or anti-CD8 antibody) and/or an epitope peptide-tetramer reagent. After fixation, the cells are subjected to membrane permeabilization and allowed to react to a dye-labeled anti-IFNγ antibody. The percentage of IFNγ-positive cells in the whole cells, T cells, or epitope peptide-tetramer-positive cells is determined through analysis using a flow cytometer or such.

b-2. Method Based on Cytokine Quantitation 2 (ELISPOT Assay)

PBMCs are plated in an anti-IFNγ antibody-immobilized 96-well MultiScreen-HA plate (Millipore Co.) Epitope peptides are aliquoted into each well, and the plate is incubated in a 5% $CO_2$ incubator at 37° C. for 20 hours. On the next day, the plate is washed, and incubated with anti-IFNγ antibody and peroxidase-labeled anti-IgG antibody in this order. Then, a peroxidase substrate is added, and IFNγ spots are visualized by color development and counted under a stereoscopic microscope.

b-3. Method Based on Cytokine Quantitation 3 (Quantitation of IFNγ Secreted to the Culture Supernatant)

PBMCs are suspended at a cell density of about $2 \times 10^6$ cells/mL in an adequate culture medium, and CTL epitope peptides of the present invention are added thereto. The cells are cultured in a 5% $CO_2$ incubator at 37° C. for 24 to 48 hours. After culture, the supernatant is collected and the concentration of IFNγ therein is determined using a commercially available ELISA kit (for example, HUMAN IFN gamma ELISA, MBL Co.).

(c) Quantitation Method 3

Quantitation is carried out using cell surface protein-specific antibodies. It is reported that expression of cell surface proteins containing for example CD107a, CD107b, CD63, and CD69 is upregulated on antigen-specific CTL upon stimulation with specific peptides. CTLs bound to a labeled antibody are stained with a labeling dye by mixing peptide-stimulated PBMCs or the like with the labeled antibody that specifically recognizes such a protein. Thus, stained CTLs are counted using a flow cytometer, microscope, or such. T cell subsets of EBV-specific CTLs can also be determined by reacting simultaneously or in succession an anti-CD3 antibody, anti-CD4 antibody, anti-CD8 antibody, or the like that has been labeled with a dye different from that of the labeled antibody at the time of reaction with the labeled antibody.

In a preferred embodiment, the quantitation methods of the present invention include, specifically, the quantitation methods described in the above (a) to (c).

Thus, preferred embodiments of the quantitation methods of the present invention are methods for quantifying EBV-specific CTLs, which include stimulating peripheral blood with the peptides of the present invention, collecting CTLs specific to the virus, and assaying a cytokine and/or chemokine, and/or cell surface molecule produced by the CTLs.

Furthermore, the MHC-tetramer (or monomer or multimer) reagent can be used to quantify specific CTLs as well as to quantify separated, purified specific CTLs as described above. In another embodiment, the present invention relates to methods for quantifying EBV-specific CTLs in peripheral blood, which include preparing MHC-tetramer reagents from the peptides of the present invention and reacting the MHC-tetramer reagents with peripheral blood.

All prior-art documents cited herein are incorporated herein by reference.

EXAMPLES

Hereinafter, the present invention is described in more detail with reference to Examples; however, it should not be construed as being limited thereto.

Example 1

Preparation of Cell Strains and Dendritic Cells

The present inventors first induced CTL clones specific to LMP1, an EBV protein, and identified LMP1-derived epitopes.

The cell strains and dendritic cells used in the experiments for identifying LMP1-derived epitopes (Examples 1 to 8) were prepared by the following methods.

The study design and purpose, which had been approved by the institutional review board of Aichi Cancer Center (Japan), were fully explained and informed consents were obtained from all the donors.

EBV-infected LCLs were prepared by known methods (Kuzushima K., et al., Blood, 94:3094-3100 (1999)) and cultured in RPMI1640 medium (Sigma Chemical Co., St. Louis, Mo., USA) supplemented with 10% fetal calf serum (PAA laboratories, Pasching, Austria), 2 mM L-glutamine, 50 U/mL penicillin, 50 μg/mL streptomycin, and 50 μg/mL kanamycin.

EBV-carrying NK cell lines, SNK-6 (Nagata H., et al., Blood, 97:708-713 (2001)), and SNK-10 (Zhang Y., et al., Br. J. Haematol., 121:805-814 (2003)) were provided by Dr. Shimizu (Tokyo Medical and Dental University, Tokyo, Japan). Another EBV-carrying NK cell line, HANK-1 (Kagami Y., et al., Br. J. Haematol., 103:669-677 (1998)), was donated by Dr. Kagami (Aichi Cancer Center Hospital, Nagoya, Japan). These three cell lines were cultured according to the methods known by those skilled in the art (Nagata H., Blood, 97:708-713 (2001)).

HEK-293T cells (American Type Culture Collection, Manassas, Va., USA) and Phoenix-GALV cells (Akatsuka Y., et al., Tissue Antigens, 59:502-511 (2002)) (gifts from Dr. Kiem, Fred Hutchinson Cancer Research Center; and Dr. Nolan, Stanford University, Stanford, Calif., USA) were cultured by known methods. Retroviral transduction of HLA genes was performed according to a known method (Kondo E., et al., J. Immunol., 169:2164-2171 (2002)).

Dendritic cells were prepared by known methods (Romani N., et al., J. Exp. Med., 180:83-93 (1994); Sallusto F., et al., J. Exp. Med., 179:1109-1118 (1994); and Dauer M., et al., J. Immunol., 170:4069-4076 (2003)). CD8$^+$ T cells were separated from PBMCs using CD8 MicroBeads (Miltenyi Biotec, Bergisch Gladbach, Germany) and stored at −135° C. until use.

CD8-depleted PBMCs were suspended in 4 mL RPMI1640 medium supplemented with 5% human serum (MP Biomedicals, Aurora, Ohio) and 2 mM L-glutamine, 50 U/mL penicillin, 50 μg/mL streptomycin, and 50 μg/mL kanamycin (DC medium) and incubated for two hours in a 6-well plate at 37° C.

Non-adherent cells were removed by gentle pipetting, and the adherent cells were cultured in DC medium containing 50 ng/mL granulocyte-macrophage colony stimulating factor (GM-CSF; Osteogenetics, Wuerzburg, Germany) and 10 ng/mL IL-4 (Osteogenetics). On days 2 and 4, half of the medium was replaced with fresh DC medium containing GM-CSF and IL-4. On day 6, dendritic cells were collected and electroporated for mRNA transduction.

B cells activated by CD40 stimulation (CD-40B) were generated according to the known methods (Kondo E., et al., J. Immunol., 169:2164-2171 (2002)) by using NIH/3T3-human CD40 ligand cells, which had been provided by Dr. Freeman of Dana-Farber Cancer Institute, Boston, Mass., USA.

Example 2

Preparation of Deletion Mutant ΔLMP1 mRNA

To generate deletion mutant ΔLMP1-expressing antigen-presenting cells, the present inventors first produced deletion mutant ΔLMP1 mRNA by using an in vitro transcription system from the pcDNA/ΔLMP1 plasmid.

To construct a 43-amino acid N-terminal deletion mutant, ΔLMP1 (Gottschalk S., Blood, 101: 1905-1912 (2003)), PCR was performed using a sense primer 5'-AAGCTTGCCAC-CATGAGTGACTGGACTGGA-3' (SEQ ID NO: 23), an antisense primer 5'-TTGAATTCTTAGTCATAGTAGCT-TAGCTGA-3' (SEQ ID NO: 24), and EBV strain B95-8 (NCBI accession no. V01555) cDNA as a template. The amino acid sequence and the oligonucleotide sequence of the deletion mutant ΔLMP1 are shown as SEQ ID NOs: 34 and 35, respectively. The resultant DNA fragment was cloned into pcDNA 3.1(+) (Invitrogen, Carlsbad, Calif., USA) using its HindIII and EcoRI restriction enzyme recognition sites (pcDNA/ΔLMP1). For constructing further C-terminal and N-terminal deletion mutants of the ΔLMP1, truncated fragments were prepared by PCR using pcDNA/ΔLMP1 as a template and inserted into the pcDNA3.1(+). To construct some plasmids encoding short LMP1 peptide fragments, each pair of complementary oligonucleotides were annealed and inserted into pcDNA3.1(+) truncated by restriction enzyme.

ΔLMP1 and cDNA of the fluorescent protein EGFP (Kondo E., et al., J. Immunol., 169:2164-2171 (2002)) were inserted into the pMSCVpuro retroviral vector (BD Biosciences Clontech, Palo Alto, Calif., USA) to generate pMSCVpuro/ΔLMP1 and pMSCVpuro/EGFP, respectively. Short hairpin RNA (shRNA) interference retrovirus vectors were constructed using the RNAi-Ready pSIREN-RetroQ vector (BD Biosciences Clontech).

To establish retrovirus-producing cells, pMSCVpuro/ ΔLMP1, pMSCVpuro/EGFP, and RNAi-Ready pSIREN-RetroQ-type various vectors were packaged in PT67 cells (BD Biosciences Clontech) using LIPOFECTAMINE™ 2000 (Invitrogen). LCL cells were infected with the retroviral supernatant containing 8 mg/L polybrene (Sigma Chemical Co.), centrifuged at 1,000×g at 32° C. for one hour, and incubated at 37° C. for two days. Thereafter, these LCL cells were cultured in the presence of 0.8 μg/mL puromycin for 14 days. Expression of EGFP and LMP1 was analyzed by flow cytometry.

Example 3

Transduction of ΔLMP1 mRNA into Cells and Verification of ΔLMP1 Expression in Cells Fragments comprising the T7 promoter region and the ΔLMP1 coding region were prepared by PCR using pcDNA/ΔLMP1 as a template. The amplified DNA was used as a template for in vitro transcription of 5'-capped mRNA. The in vitro transcription of 5'-capped mRNA was performed using a mMESSAGE mMACHINE kit (Ambion, Austin, Tex., USA).

The 3' polyA tail was added using polyA polymerase (Ambion) followed by purification with an RNeasy kit (Qiagen, Tokyo Japan).

Prior to electroporation, the dendritic cells and CD40-B cells were washed twice with serum-free RPMI1640 medium and adjusted to a final concentration of $2.5 \times 10^7$ cells/mL. The cells in 40 μL RPMI 1640 medium were mixed with 20 μg of mRNA, and electroporated in a 2 mm cuvette using an Electro Square Porator ECM 830 (Harvard Apparatus, Holliston, Mass.). The conditions were 450 V and 500 μS for dendritic cells and 350 V and 350 μS for CD40-B cells.

After electroporation, the dendritic cells were cultured in DC medium supplemented with GM-CSF and IL-4 for three hours, then added with TNF-α (PeproTech, Rocky Hill, N.J., USA), IL-1β (PeproTech), and $PGE_2$ (Cayman Chemical, Ann Arbor, Mich., USA) for maturation. CD40-B cells were immediately seeded onto irradiated NIH/3T3-human CD40 ligand cells and used as antigen-presenting cells after 36 to 48 hours.

Intracellular staining of LMP1 antigen was performed by known methods with a slight modification (Gottschalk S., et al., Blood, 101: 1905-1912 (2003)). Specifically, the cells transduced by electroporation were collected and fixed with 4% paraformaldehyde-containing PBS for ten minutes at room temperature. After washing with PBS, the cells were permeabilized with IC Perm (BioSource International, Camarillo, Calif., USA) and reacted with a monoclonal antibody which recognizes LMP1 C-terminus (CS1-4, DAKO Cytomation, Glostrup, Denmark) for 30 minutes at 4° C. After washing with PBS, the cells were stained with fluorescein isothiocyanate (FITC)-labeled anti-mouse IgG (H+L) (Immunotech, Marseille, France) for 30 minutes at 4° C. The stained cells were analyzed by FACSCallibur (BD Biosciences, San Jose, Calif., USA) using CellQUEST software (BD Biosciences).

Figure 1:
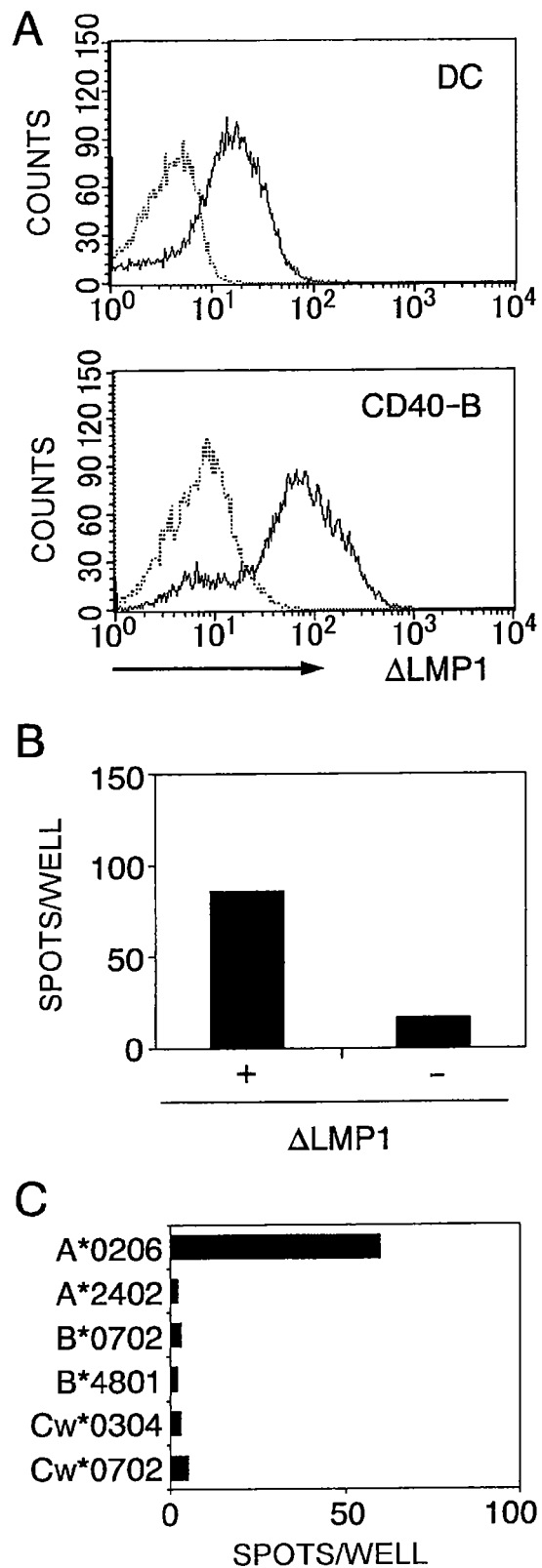
FIG. 1 shows transduction of ΔLMP1 mRNA into dendritic cells and CD40-B cells, ΔLMP1 expression, and CTL induction.

ΔLMP1 expression was analyzed by flow cytometry. Seventy percent or more of both the dendritic cells and CD40-B cells were positive for ΔLMP1 (FIG. 1A). Eighty percent or more of the cells were viable at 36 to 48 hours post electroporation (data not shown).

These cells were used as antigen-presenting cells to generate LMP1-specific T cells from five seropositive donors.

Example 4

Induction of ΔLMP1-specific CTL Clones Using ΔLMP1 mRNA-transduced Dendritic Cells Next, ΔLMP1-specific CTL clones were induced according to the following procedures.

Stored $CD8^+$ T cells were thawed, washed, and co-cultured with irradiated (33Gy) autologous ΔLMP1 mRNA-transduced dendritic cells in 2 mL RPMI1640 medium supplemented with 10% human serum, 2 mM L-glutamine, 50 U/mL penicillin, 50 μg/mL streptomycin, 50 μg/mL kanamycin, 25 ng/mL IL-7 (R&D Systems, Minneapolis, Minn., USA), and 5 ng/mL IL-12 (R&D systems) at 5% $CO_2$ in a humidified incubator. On days 8 and 15, T cells were stimulated again with ΔLMP1 mRNA-transduced, γ-irradiated dendritic cells and CD40-B cells, respectively. One day after the each stimulation, IL-2 (Shionogi, Osaka, Japan) was added to a final concentration of 20 U/mL. To establish T cell clones, limiting dilution of polyclonal CTLs was performed using round-bottomed 96-wells according to a known method (Kuzushima K., et al., Blood, 98:1872-1881 (2001)).

After two weeks of culture, growing wells were split into three and a part of each of them were used as effector cells in the CTL assay against either ΔLMP1 mRNA- or EGFP mRNA-transduced autologous CD40-B cells. Wells were scored as positive when the counts per minute from ΔLMP1 mRNA-transduced CD40-B cells exceeded the mean counts per minute from EGFP mRNA-transduced CD40-B cells by 3 SD. Positive wells were transferred into flasks and expanded by the known methods (Kuzushima K., et al., Blood, 98:1872-1881 (2001)).

Peripheral $CD8^+$ T cells were stimulated with ΔLMP1 mRNA-transduced, γ-irradiated dendritic cells and CD40-B cells three times and assayed by ELISPOT to examine specificity of T cell lines.

ELISPOT assays were performed by known methods (Kuzushima K., et al., Blood, 94:3094-3100 (1999); Kondo E., et al., J. Immunol., 169:2164-2171 (2002); and Kuzushima K., et al., Blood, 98:1872-1881 (2001)). Specifically, CD8 T cells were co-cultured with various stimulators in wells of Multi-screen-HA plates (MAHA S4510; Millipore, Billerica, Mass., USA) coated with anti-human interferon-γ (IFNγ) monoclonal antibody (Pierce Biotechnology, Philadelphia, Pa., USA).

As stimulators, HLA-A*0206-positive or -negative LCLs ($1 \times 10^5$ cells/well) or HLA-A*0206-expressing HEK-293T (A0206-293T) cells ($5 \times 10^4$ cells/well) transfected with plasmids using Lipofectamin 2000 (Invitrogen) were seeded into each well 48 hour before T cell addition. For peptide titration assays, several concentrations of synthetic peptides (Greiner, Frickenhausen, Germany) were pulsed to A0206-293T cells for one hour at room temperature. After probing with anti-rabbit polyclonal IFNγ antibody (Pierce Biotechnology) and reacting with peroxidase-labeled anti-rabbit IgG antibody (Genzyme, Cambridge, Mass., USA) for spot visualization, the plates were washed and dried. IFNγ spots were enumerated using a stereoscopic microscope.

As a result, it was found that the polyclonal T cells from one out of five donors specifically secreted IFNγ in response to ΔLMP1 mRNA-transduced autologous CD40-B cells, but not to non-transduced CD40-B cells (FIG. 1B).

The present inventors established a T-cell clone, designated as H7, by limiting dilution of the bulk CTL line. The H7 lysed ΔLMP1 mRNA-transduced autologous CD40-B cells but not EGFP mRNA-transduced CD40-B cells (data not shown). HLA genotyping revealed that the blood donors had HLA-A*0206, A*2402, B*0702, B*4801, Cw*0304, or Cw*0702. To identify HLA molecules presenting CTL epitopes, fully HLA-mismatched LCLs retrovirally transduced with each HLA gene were used. H7 produced IFNγ spots when incubated with LCLs transduced with HLA-A*0206, demonstrating HLA-A*0206 to be an epitope-presenting molecule (FIG. 1C).

Example 5

Identification of LMP1 Epitope

There have been no reports of HLA-A*0206-restricted LMP1-derived epitopes with the exception of the peptide, YLLEMLWRL (SEQ ID NO: 25) which belongs to HLA-A2 supertype. Since H7 did not produce IFNγ with the peptide YLLEMLWRL (SEQ ID NO: 25) (data not shown), the present inventors tried identification of an epitope recognized by H7.

The present inventors electroporated autologous CD40-B cells with some C-terminal-truncated ΔLMP1 mRNA, and tested recognition by the H7 in ELISPOT assays. As demonstrated in FIG. 2A, antigenicity was lost on C-terminal truncation between amino acid residues 70 and 77, indicating the C-terminus of the epitope to be located between amino acid residues 71 and 77.

Hereinafter, A0206-293T cells transfected with plasmids comprising C-terminal-truncated ΔLMP1 mRNA were used because the plasmid-transduced A0206-293T cells are more easily prepared than CD40-B cells and mRNA. With the A0206-293T cells as antigen-presenting cells, antigenicity was lost when C-terminal truncation was between amino acid residues 77 and 88 (data not shown). The reason for the discrepancy with the data using CD40-B cells is unknown. Here, LMP1 truncated with the C-terminus at amino acid residue 88 was used. A series of plasmids with further deletions on the N-terminal side were prepared and analyzed (FIG. 2B). The shortest stimulatory fragment was identified as residues 64-83. To precisely define the N- and C-terminal ends, further truncation was performed in the vicinity.

As demonstrated in FIG. 2C, a plasmid encoding amino acid residues 64-71 (I I I L I I F I, SEQ ID NO: 18), exhibited the strongest antigenicity, while deletion of either residue 64 or 71 completely abolished the antigenicity.

Although amino acid residues 64-71 may constitute the minimal epitope for H7, it is possible that the N-terminus methionine encoded by the start codon of the expression vector substitutes for isoleucine at position 63 to meet structural requirements for MHC binding and H7 recognition. To elucidate this point, a synthetic 8-mer peptide (amino acid residues 64-71, I I I L I I F I, SEQ ID NO: 18), and a 9-mer peptide (amino acid residues 63-71, I I I I L I I F I, SEQ ID NO: 1) were pulsed on the A0206-293T cells and the H7 reactivity was tested in ELISPOT assays. As demonstrated in FIG. 2D, only the 9-mer peptide was recognized by H7, indicating that the minimal epitope starts from isoleucine at position 63.

Example 6

Assessment of the Importance of the Immunoproteasome Subunit ip-LMP7 for LMP1 63-71 Epitope Generation Regarding antigen processing in LMP1-transduced cells, two discrepancies were observed in the ELISPOT assays:

(1) H7 recognized CD40-B cells transduced with full-length ΔLMP1 mRNA (FIG. 2A) but not A0206-293T cells transduced with the plasmid expressing the same structure; and
(2) H7 recognized CD40-B cells transduced with truncated ΔLMP1 mRNA encoding amino acid residues 44-77 (FIG. 2A) but not A0206-293T cells transduced with the plasmid expressing the same sequence.

Here, the present inventors hypothesized that different machinery for antigen processing resulted in these discrepancies in generation of the LMP1 epitope. A0206-293T cells predominantly express standard proteasomes while in CD40-B cells and LCL cells immunoproteasomes are dominant (Frisan T., et al., Int. J. Cancer, 88:881-888 (2000); and Morel S., et al., Immunity, 12:107-117 (2000)). Standard proteasomes play a critical role in the antigen processing pathway, and exposure of cells to IFNγ during immune response alters the proteasome activity qualitatively and quantitatively by induction of newly synthesized immunoproteasome β subunits, such as low molecular weight protein (ip-LMP) 2 and ip-LMP7, assembling immunoproteasomes.

To determine whether the effects of immunoproteasomes are critical for epitope processing, the present inventors used LCLs in which expression of the immunoproteasome subunit was inhibited. Tip-LMP2 and ip-LMP7 were used as siRNA targets because they were known to be crucial molecules in the generation of epitopes from transmembrane proteins such as EBV-LMP2 (Lautscham G., et al., J. Virol., 77:2757-2761 (2003)) and MAGE-3 (Levitskaya J., et al., Nature, 375:685-688 (1995)).

The following siRNA targets were selected in this study. Specifically, for ip-LMP2, AAGUGAAGGAGGUCAG-GUAUA (SEQ ID NO: 26) was selected and for ip-LMP7, AGAUUAACCCUUACCUGCUTT (SEQ ID NO: 27).

The shRNA constructs comprise a TTCAAGAGA-loop separating the sense and antisense sequences followed by a 5T termination signal. These constructs were synthesized as two complementary DNA oligonucleotides, annealed, and inserted between the BamHI and EcoRI restriction enzyme recognition sites of the vector. In addition, a negative control siRNA (BD Biosciences Clontech) was inserted into the same vector and used as a control. The cloned genes were sequenced to verify their identity.

Expression of ip-LMP2 and ip-LMP7 was assessed by a known method, i.e., Western blotting (Schwarz K., et al., J. Immunol., 165:768-778 (2000); and Tajima K., et al., Int. J. Cancer, 110:403-412 (2004)).

As shown in FIG. 3A, expression of ip-LMP2 and ip-LMP7 was significantly reduced in LCL cells transfected with the corresponding shRNA vector. The effect of gene silencing on the LMP1 epitope generation was assessed using ELISPOT assays. Interestingly, production of IFNγ spots by the H7 clone was significantly reduced when stimulated with ip-LMP7-silenced LCLs, whereas suppression of ip-LMP2 expression had negligible effects (FIG. 3B).

These data indicate that ip-LMP7 is essential for processing and presentation of the LMP1 epitope.

Example 7

Determination of Cytotoxic Activity of LMP1-specific CTL Clones Against LCL Cells Next, cytotoxic activities of H7 on LCLs were explored. CTL assays were conducted according to the following procedures. Target cells were labeled with 50 µCi chromium ($^{51}$Cr) for one and a half hours at 37° C., washed, and mixed with CTLs at the indicated effector:target ratios in 96-well plates. After incubation for 4 or 16 hours at 37° C., the radioactivity in the supernatants was counted with a γ-counter. The percentage of specific $^{51}$Cr release was calculated as follows: 100×{(experimental release)−(spontaneous release)}/{(maximum release)−(minimum release)}.

Standard CTL assays revealed that H7 could not efficiently lyse HLA-A*0206-positive LCLs with a four hour incubation (data not shown) but lysed autologous and HLA-A*0206-positive allogenic LCL cells after 16 hours (FIG. 4A) suggesting insufficient LMP1 expression in the LCLs for H7-mediated cell lysis in the four-hour CTL assay.

Thus, the experiments were conducted with LCLs with forced expression of ΔLMP1 as target cells as shown in FIG. 4B. H7 specifically lysed ΔLMP1-expressing LCLs, but not EGFP-expressing LCLs in the four-hour CTL assay.

Example 8

Assessment of Cytotoxic Activities of LMP1-specific CTL Clones Against EBV-infected NK Cell Lines EBV LMP1 is expressed in LCL cells with other proteins as latency III and also in NK/T cells as latency II (Zhang Y., et al., Br. J. Haematol., 121:805-814 (2003)). Thus, the cytotoxic activity of H7 cells against EBV-positive NK cell lines (Nagata H., et al., Blood, 97:708-713 (2001); Zhang Y., et al., Br. J. Haematol., 121:805-814 (2003); and Kagami Y., et al., Br. J. Haematol., 103:669-677 (1998)), as representatives of EBV latency II malignancies, was examined. Among the three LMP1-expressing NK cell lines examined, two were positive for HLA-A*0206. As shown in FIG. 5A, H7 lysed one of the HLA-A*0206-positive lines (SNK-10) but not the other (SNK-6) or HLA-A*0206-negative lines (HANK-1). HLA-A*0206-transduced HANK-1 cells were specifically lysed by H7 cells (FIG. 5B). Since the epitope peptide-pulsed SNK-6 cells were efficiently lysed by H7 (FIG. 5A), SNK-6 cells might have a mutation in the LMP1 epitope. The present inventors sequenced genomic DNA binding with the LMP1 epitope. All three EBV-positive NK cell lines demonstrated the same mutations which do not affect the amino acid sequence from positions 55 to 80 (data not shown).

Example 9

Preparation of Cell Strains and Dendritic Cells

The present inventors next induced CTL clones specific to EBNA1 among EBV proteins, and identified EBNA1-derived epitopes.

The cell strains and dendritic cells used in the experiments for identifying EBNA1-derived epitopes (Examples 9 to 16) were prepared by the following methods.

The study design and purpose, approved by the institutional review board of Aichi Cancer Center, were fully explained to all the blood donors and informed consents were obtained.

CD40-activated B cells (CD40-B) were generated from PBMCs of the blood donors according to a known method (Schultze J. L., et al., J. Clin. Invest., 100:2757-2765 (1997); and Kondo E., et al., J. Immunol., 169:2164-2171 (2002)). Briefly, PBMCs were cultured with irradiated CD40L-transfected NIH/3T3 cells (hereinafter referred to as t-CD40L; provided by Dr. Gordon Freeman, Dana-Farber Cancer Institute, Boston), recombinant IL-4 (Genzyme, Cambridge, Mass.), and cyclosporine A (Sandoz, Basel, Switzerland) in the culture medium. Expanding CD40-B was stimulated twice a week.

EBV-retaining LCLs were prepared by differentiating PBMCs with B95-8 cell culture supernatant by a known method (Kuzushima K., et al., Blood, 94:3094-3100 (1999)) and cultured in RPMI1640 medium (Sigma Chemical Co., St. Louis, Mo.) supplemented with 10% fetal calf serum, 2 mM L-glutamine, 50 U/mL penicillin, 50 µg/mL streptomycin, and 50 µg/mL kanamycin.

Dendritic cells were prepared by a known method (Romani N., et al., J. Exp. Med., 180:83-93 (1994); Sallusto F., et al., J. Exp. Med., 179:1109-1118 (1994); and Dauer M., et al., J. Immunol., 170:4069-4076 (2003)). Specifically, CD8$^+$ T cells were isolated from PBMCs using CD8 MicroBeads (Miltenyi Biotec, Bergisch Gladbach, Germany) and stored at −135° C.

The CD8-depleted PBMCs were suspended in 4 mL RPMI1640 medium supplemented with 5% human serum (MP Biomedicals, Aurora, Ohio) and 2 mM L-glutamine, 50 U/mL penicillin, 50 µg/mL streptomycin, and 50 µg/mL kanamycin (DC medium) and incubated for two hours in 6-well plates at 37° C.

Non-adherent cells were removed by gentle pipetting, and adherent cells were cultured in DC medium containing 50 ng/mL granulocyte-macrophage colony stimulating factor (GM-CSF, Osteogenetics, Wuerzburg, Germany) and 10 ng/mL IL-4 (Osteogenetics). On days 2 and 4, half of the medium was replaced with fresh DC medium containing GM-CSF and IL-4. On day 6, dendritic cells were collected and electroporated for mRNA transduction.

Example 10

Production of Full-length EBNA1 mRNA

To generate EBNA1-expressing antigen-presenting cells, the present inventors produced full-length EBNA1 mRNA with a polyA tail using an in vitro transcription system from the pcDNA/EBNA1 plasmid.

To generate in vitro transcribed EBNA1 mRNA, a pcDNA/EBNA1 vector was constructed. The coding sequence for EBNA1 was obtained by extraction of total RNA from B95.8-transformed LCLs using the RNeasy kit (Qiagen, Hilden, Germany). The amino acid sequence and the oligonucleotide sequence of EBNA1 are shown as SEQ ID NOs: 36 and 37, respectively. After reverse transcription, EBNA1 cDNA was amplified by PCR with the following specific primers: forward primer, 5'-AAGCTTGCCACCATGTCTGAC-GAGGGGCCAGGTACAG (SEQ ID NO: 28); reverse primer, 5'-GAATTCTCACTCCTGCCCTTCCTCACCCTC (SEQ ID NO: 29).

The full-length EBNA1 fragment was then inserted into pcDNA3.1(+) (Invitrogen, Carlsbad, Calif.) using its HindIII and EcoRI sites. The clones were sequenced to verify the EBNA1 transduction. Resulting plasmid DNA was linearized and transcribed in vitro using the mMESSAGE and mMACHINE kit (Ambion, Austin, Tex.). A 3' polyA tail was added to EBNA1 mRNA using polyA polymerase (Ambion), followed by purification with an RNeasy kit. The purified mRNA was verified using the Reliant RNA gel system (Cambrex, Rockland, Me.).

The yield of capped mRNA was found to be low, probably due to the GAr region comprising GC-rich sequences. The problem of yield was not fully overcome by the change of reaction temperature or by adding single-stranded binding protein to the reaction mixture (data not shown). However, the amount of mRNA was sufficient and seen as a single band on the gel (FIG. 6A).

Example 11

Transduction of Full-length EBNA1 mRNA into Cells and Verification of EBNA1 Expression in Cells Dendritic cells and CD40-B cells were transduced with full-length EBNA1 mRNA by electroporation. First, they were washed twice with serum-free RPMI1640 medium and suspended at a final concentration of $2.5 \times 10^7$ cells/mL. After mixing with 20 µg of mRNA in 40 µL of RPMI1640 medium, they were electroporated in a 2 mm cuvette using the Electro Square Porator ECM 830 (Harvard Apparatus, Holliston, Mass.), under conditions of 450 V and 500 µS for dendritic cells and 350 V and 350 µS for CD40-B cells.

Dendritic cells were subsequently cultured in DC medium supplemented with GM-CSF and IL-4 for three hours, and further with TNF-α (PeproTech, Rocky Hill, N.J., USA), IL-1β (PeproTech), and $PGE_2$ (Cayman Chemical, Ann Arbor, Mich.) for maturation. CD40-B cells were immediately seeded onto irradiated NIH/3T3-human CD40 ligand cells, and after 36 to 48 hours, these cells were used as antigen-presenting cells.

Next, EBNA1 was stained by the following process. EBNA1 mRNA-transduced CD40-B cells were collected and fixed with 4% paraformaldehyde in phosphate-buffered saline (PBS) for ten minutes at room temperature. After washing with PBS, the cells were permeabilized with PBS containing 0.5% Tween-20 and reacted with anti-EBNA1 rabbit polyclonal antibody (provided by Dr. Tatsuya Tsurumi, Aichi Cancer Center Research Institute, Nagoya, Japan) for 30 minutes at 4° C. After washing with PBS, the cells were stained with FITC-labeled goat anti-rabbit IgG (Beckman Coulter, Fullerton, Calif.) for 30 minutes at 4° C. The stained cells were analyzed by FACSCallibur (BD Biosciences, San Jose, Calif.) using CellQUEST software (BD Biosciences).

EBNA1 expression was detected on most CD40-B cells, although the mean fluorescent intensity appeared to be low (FIG. 6B). Dendritic cells were not available for this analysis due to the limited number of cells obtained from the donors' PBMCs.

Example 12

Induction of EBNA1-specific CTL Clones Using EBNA1 mRNA-transduced Dendritic Cells Monocyte-derived dendritic cells of a healthy donor were transduced with full-length EBNA1 mRNA by electroporation and maturation was induced by addition of a mixture of inflammatory cytokines.

EBNA1-specific CTL clones were induced according to the following procedures.

The stored $CD8^+$ T cells were thawed and cultured in 200 µL RPMI1640 medium containing 10% human serum, 2 mM L-glutamine, 50 U/mL penicillin, 50 µg/mL streptomycin, and 50 µg/mL kanamycin (referred as CTL medium) and further supplemented with 5 ng/mL IL-7 (R&D Systems, Minneapolis, Minn.) and 5 ng/mL IL-12 (R&D systems) at 5% $CO_2$ in a humidified incubator. On day 8, 16, and 23, T cells were stimulated with EBNA1 mRNA-transduced, γ-irradiated dendritic cells. One day after each restimulation, IL-2 (Shionogi, Osaka, Japan) was added to a final concentration of 20 U/mL. To establish T cell clones, limiting dilution of polyclonal CTLs was performed (Kuzushima K., et al., Blood, 98:1872-1881 (2001)).

Polyclonal $CD8^+$ T cells were seeded at 1 cell/well in round-bottom 96-well plates containing CTL medium with a monoclonal antibody (mAb) specific to CD3 (30 ng/mL, Ortho Biotech, Bridgewater, N.J.) γ-irradiated $1 \times 10^5$ PBMCs (33Gy), and $2 \times 10^4$ LCLs (55Gy). Next day, IL-2 was added to each well (50 U/mL). After two weeks of culture, wells with a good growth were split into two and used as effectors in ELISPOT assays against either autologous EBNA1 mRNA-transduced CD40-B cells or autologous LCLs.

After three rounds of stimulation, aliquots of each microcultures were tested for their ability to secrete IFNγ specifically upon contact with autologous CD40-B cells transduced with EBNA1 mRNA in the ELISPOT assay.

ELISPOT assays were performed by a known method (Kuzushima K., et al., Blood, 101:1460-1468 (2003)). Specifically, CD8 T cells were co-cultured with various stimulators in wells of Multiscreen-HA plates (Millipore, Billerica, Mass.) coated with anti-human interferon-γ (IFNγ) monoclonal antibody (Pierce Biotechnology, Philadelphia, Pa.). As stimulators, (A) autologous EBNA1 mRNA-transduced CD40-B cells or non-transduced CD40-B cells and (B) autologous or allogenic LCLs ($1 \times 10^5$ cells/well) were seeded into each well. For peptide titration assays and the overlapping peptide assay described below, serial concentrations of synthetic peptides were added to autologous CD40-B cells for one hour at room temperature.

After reacting with anti-human IFNγ rabbit polyclonal antibody (Pierce Biotechnology), followed by addition of peroxidase-labeled anti-rabbit immunoglobulin antibody (Genzyme, Cambridge, Mass.) and substrate, the plates were washed and dried. IFNγ spots were enumerated under a stereoscopic microscope.

EBNA1-specific CTLs were present in 32 out of 36 wells (data not shown). CTL clones B5 and C6 were established by limiting dilution. The clones were expanded with anti-CD3 monoclonal antibody, irradiated feeder cells, and IL-2.

These clones recognize EBNA1 mRNA-transduced autologous CD40-B cells and LCLs, but not non-transduced autologous CD40-B cells and HLA-mismatched allogenic LCLs (FIG. 7).

Example 13

Identification of Antigen-presenting HLA Molecules

The donors were genetically typed as HLA-A*2402, A*3101, B*1507, B*3501, or Cw*0303. To identify the antigen-presenting HLA molecules, a panel of partially-HLA-matched LCLs was used to stimulate clone B5 or C6 to generate IFNγ. In addition to autologous LCLs, allogenic LCLs expressing HLA-B*3501 were recognized by CTL clone C6 (FIG. 8A). LCLs with HLA-Cw*0303 or -Cw*0304 were recognized by clone B5 (FIG. 8B). This demonstrates that HLA-B*3501 is a putative restriction factor for clone C6 recognition, while both HLA-Cw*0303 and Cw*0304 act for clone B5.

Example 14

Identification of EBNA1 Antigen Peptides

To identify the epitope region, clones B5 and C6 were stimulated with autologous CD40-B cells incubated with sets of peptides having 20 amino acids. The peptides used in the present invention were purchased from Bio-Synthesis, Inc. (Lewisville, Tex.). Since the primary structure of GAr is not likely to be contained in MHC class I epitopes, the present inventors excluded this part from the epitope source. The whole EBNA1 protein sequence, excluding the GAr domain, was covered by a set of peptides (total of 56 peptides) overlapping by 13 amino acids.

Peptide #24 was recognized by clone C6 (FIG. 9). Regarding the HLA-B*3501-restricted epitope, HPVGEADYFEY (SEQ ID NO: 30) has been reported previously (Blake N., et al., Immunity, 7:791-802 (1997)).

Since this epitope sequence is located in the center of peptide #24 (402-421) (FIG. 10A), the present inventors postulated that clone C6 should recognize HPVGEADYFEY (SEQ ID NO: 30) as its epitope peptide.

In the case of clone B5, two overlapping peptides #38 (500-519) and #39 (507-526) were recognized (FIG. 9), sharing the 13 amino acid sequence VFVYGGSKTSLYN (SEQ ID NO: 31) underlined in FIG. 10B. To predict the optimal epitope binding to HLA-Cw*0303, the program SYFPEITHI (on the world wide web at syfpeithi.de; Rammensee H., et al., Immunogenetics, 50:213-219 (1999)) was applied. In addition, potential epitope peptides, VYGGSKTSL (509-517) (SEQ ID NO: 22), FVYGGSKTSL (508-517) (SEQ ID NO: 3), and VFVYGGSKTSL (507-517) (SEQ ID NO: 2) were synthesized, as predicted with the program SYFPEITHI.

Because the anchor leucine at the C-terminus and the auxiliary anchors valine and tyrosine at the third position of epitopes were predicted by the program, the present inventors examined the 11-mer (VFVYGGSKTSL; SEQ ID NO: 2) and the 10-mer (FVYGGSKTSL; SEQ ID NO: 3) peptide (FIG. 10B).

Half maximal recognition of the peptide-supplemented target cells was obtained with 5 to 10 nM of the 10-mer peptide and 1 to 5 nM of the 11-mer peptide (FIG. 10C). The 9-mer peptide (VYGGSKTSL; SEQ ID NO: 22) was not recognized even with much higher concentrations.

Since the peptide dilution assay did not disclose optimal epitope length for the clone B5 (FIG. 10C), the present inventors decided to use a structural approach to resolve the same question. To this end, the present inventors produced fluorescent-labeled tetramers incorporating the 10-mer peptide FVYGGSKTSL (SEQ ID NO: 3) or the 11-mer VFVYGGSKTSL (SEQ ID NO: 2).

The tetramers were produced and stained by the following process:

HLA-Cw*0303 and -Cw*0304 cDNA clones were used as templates to amplify sequences encoding extracellular domains of HLA-Cw*0303 and -Cw*0304 heavy chains with primers C03F (5'-AACCATGGGCAGCCATTCTATGCGC-TATTTTTACACCGCTGTGTCCCGGC-3'; SEQ ID NO: 32) and C03R (5'-AAGGATCCTGGCTCCCATCT-CAGGGTGAGG-3'; SEQ ID NO: 33).

C03F comprises several base substitutions designed to optimize protein expression in *E. coli* BL21 (DE3) pLysS. The PCR product was digested with NcoI and BamHI and cloned into a vector. This vector comprises a BirA biotinylation site in the 3' end of the HLA sequence.

Recombinant HLA-Cw*0303 and Cw*0304 molecules were folded in vitro with β2-microglobulin and peptides FVYGGSKTSL (SEQ ID NO: 3) or VFVYGGSKTSL (SEQ ID NO: 2). Soluble complexes, purified by gel filtration, were biotinylated using the BirA enzyme (Avidity LLC, Denver, Colo.).

Phycoerythrin (PE)-labeled tetramers were produced by mixing these biotinylated complexes with PE-labeled streptavidin (Molecular Probes, Carlsbad, Calif.).

Tetramer staining was performed as follows. CTL clones ($2\times10^5$) were incubated with tetramers at a concentration of 20 μg/mL and FITC-labeled anti-CD8 monoclonal antibody (Caltag, Burlingame, Calif.) at 4° C. for 15 minutes. After washing twice, stained cells were fixed in 0.5% paraformaldehyde and analyzed by flow cytometry.

As shown in FIG. 11, these tetramers specifically bound to CTL clone B5. However, the tetramer incorporating 10-mer peptide demonstrated higher avidity for the B5 clone than that incorporating 11-mer peptide, suggesting the 10-mer peptide FVYGGSKTSL (SEQ ID NO: 3) to be the minimal and optimal epitope for the CTL. Moreover, clone B5 strongly bound to the HLA-Cw*0304 tetramer incorporating 10-mer peptide, showing results similar to data of FIG. 8A.

Example 16

Assessment of the Inhibitory Effect of EBNA1-specific CTLs on EBV-infected B Cell Growth Clones B5 and C6 did not lyse autologous LCLs in the chromium release assay (data not shown). Here, the experiments were performed to assess whether these EBNA1-specific CTLs could affect the long-term growth and survival of EBNA1-expressing LCLs.

Autologous and allogenic LCLs with or without the restricting HLA molecules were seeded in 96-well plates in the presence or absence of corresponding CTLs.

Outgrowth inhibition assays were performed according to a known method with some modifications (Lee S. P., et al., J. Exp. Med., 199:1409-1420 (2004)). Target LCL cells were seeded into round-bottom 96-well plates at $2\times10^4$ cells/well in triplicates. EBNA1-specific CTL clones ($1\times10^4$ cells/well) or CTL medium alone as a control were added to target cell culture medium. The medium was maintained weekly by changing half of the medium and B cell characteristics were verified by staining with PE-cyanin 5-labeled anti-CD19 and PE-labeled anti-CD8 monoclonal antibody (Beckman Coulter) and flow cytometry analysis. The culture medium was then assayed for LCL outgrowth after four weeks.

At the end, LCL outgrowth was assessed by microscopic inspection, and verified by CD19 expression by flow cytometry.

As shown in FIG. 12, both CTL clones clearly inhibited outgrowth of not only autologous LCLs but also allogenic LCLs with restricting HLA, suggesting that these CTL clones have ability to inhibit outgrowth of EBV-positive cells with latency type III.

Industrial Applicability

The present invention succeeded in identifying EBV-specific CTL epitope peptides. The peptides have a function capable of efficiently inducing EBV-specific CTLs. Thus, the peptides and nucleotides encoding them are useful as vaccines (active immunotherapeutic agents) for treating or preventing EBV infection or EBV-positive cancers. When used as a vaccine, the epitope peptides provided by the present invention can induce EBV-specific CTLs in vivo and enable maintenance of the immunity against EBV infection. The present invention also enables safe and efficient artificial induction and growth of EBV-specific CTLs in biological samples, such as peripheral blood, ex vivo without infecting with EBV. The cells can be used in cell immunotherapy. Furthermore, the present invention can be used for testing immunity against EBV, and thus provides diagnostic and therapeutic methods which are effective for EBV infection.

Alternatively, CTLs induced by the epitope peptides of the present invention specifically lyse EBV-infected cells and have the function of inhibiting the growth of the cells. Thus, the CTLs are very useful as an ingredient of passive immunotherapeutic agents.

Furthermore, EBV-specific CTLs can be quantified by using the epitope peptides. It is important to know whether EBV-specific CTLs are present in peripheral blood of high-risk patients, because such information is useful for infection management, including the proper use of antiviral agents and immunosuppressants.

The invention claimed is:

1. An isolated Epstein-Barr virus-specific cytotoxic T cell epitope peptide, which binds an HLA Class I molecule and which consists of an amino acid sequence as shown in SEQ ID NO: 1.

2. A vaccine for treating or preventing Epstein-Barr virus infection, which comprises as an active ingredient the peptide of claim 1.

3. A method for inducing an Epstein-Barr virus-specific cytotoxic T cell response, which comprises contacting a cytotoxic T cell with the peptide of claim 1.

4. The method of claim 3, further comprising contacting the peptide of claim 1 with a peripheral blood mononuclear cell in a culture medium containing plasma.

* * * * *

UNITED STATES PATENT AND TRADEMARK OFFICE
CERTIFICATE OF CORRECTION

PATENT NO. : 8,481,051 B2
APPLICATION NO. : 12/091705
DATED : July 9, 2013
INVENTOR(S) : Kiyotaka Kuzushima et al.

It is certified that error appears in the above-identified patent and that said Letters Patent is hereby corrected as shown below:

Title Page: Item 73 should read Assignee: Medical and Biological Laboratories Co., Ltd., Nagoya-shi, Aichi (JP); Aichi Prefecture, Aichi (JP)

Signed and Sealed this
Fourth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,481,051 B2
APPLICATION NO. : 12/091705
DATED : July 9, 2013
INVENTOR(S) : Kuzushima et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1231 days.

Signed and Sealed this
Twenty-sixth Day of May, 2015

Michelle K. Lee
*Director of the United States Patent and Trademark Office*

SEQUENCE LISTING

```
<160> NUMBER OF SEQ ID NOS: 38

<210> SEQ ID NO 1
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 1

Ile Ile Ile Ile Leu Ile Ile Phe Ile
1               5

<210> SEQ ID NO 2
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 2

Val Phe Val Tyr Gly Gly Ser Lys Thr Ser Leu
1               5                   10

<210> SEQ ID NO 3
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 3

Phe Val Tyr Gly Gly Ser Lys Thr Ser Leu
1               5                   10

<210> SEQ ID NO 4
<211> LENGTH: 45
<212> TYPE: PRT
<213> ORGANISM: Artificial
<220> FEATURE:
<223> OTHER INFORMATION: An artificially synthesized peptide sequence

<400> SEQUENCE: 4

Met Ser Asp Trp Thr Gly Gly Ala Leu Leu Val Leu Tyr Ser Phe Ala
1               5                   10                  15

Leu Met Leu Ile Ile Ile Ile Leu Ile Ile Phe Ile Phe Arg Arg Asp
            20                  25                  30

Leu Leu Cys Pro Leu Gly Ala Leu Cys Ile Leu Leu Met
        35                  40                  45

<210> SEQ ID NO 5
<211> LENGTH: 35
<212> TYPE: PRT
<213> ORGANISM: Artificial
<220> FEATURE:
<223> OTHER INFORMATION: An artificially synthesized peptide sequence

<400> SEQUENCE: 5
```

```
Val Leu Tyr Ser Phe Ala Leu Met Leu Ile Ile Ile Leu Ile Ile
1               5                   10                  15

Phe Ile Phe Arg Arg Asp Leu Leu Cys Pro Leu Gly Ala Leu Cys Ile
            20                  25                  30

Leu Leu Met
        35

<210> SEQ ID NO 6
<211> LENGTH: 30
<212> TYPE: PRT
<213> ORGANISM: Artificial
<220> FEATURE:
<223> OTHER INFORMATION: An artificially synthesized peptide sequence

<400> SEQUENCE: 6

Ala Leu Met Leu Ile Ile Ile Leu Ile Ile Phe Ile Phe Arg Arg
1               5                   10                  15

Asp Leu Leu Cys Pro Leu Gly Ala Leu Cys Ile Leu Leu Met
            20                  25                  30

<210> SEQ ID NO 7
<211> LENGTH: 25
<212> TYPE: PRT
<213> ORGANISM: Artificial
<220> FEATURE:
<223> OTHER INFORMATION: An artificially synthesized peptide sequence

<400> SEQUENCE: 7

Ile Ile Ile Leu Ile Ile Phe Ile Phe Arg Arg Asp Leu Leu Cys Pro
1               5                   10                  15

Leu Gly Ala Leu Cys Ile Leu Leu Met
            20                  25

<210> SEQ ID NO 8
<211> LENGTH: 20
<212> TYPE: PRT
<213> ORGANISM: Artificial
<220> FEATURE:
<223> OTHER INFORMATION: An artificially synthesized peptide sequence

<400> SEQUENCE: 8

Ile Phe Ile Phe Arg Arg Asp Leu Leu Cys Pro Leu Gly Ala Leu Cys
1               5                   10                  15

Ile Leu Leu Met
            20

<210> SEQ ID NO 9
<211> LENGTH: 20
<212> TYPE: PRT
<213> ORGANISM: Artificial
<220> FEATURE:
<223> OTHER INFORMATION: An artificially synthesized peptide sequence

<400> SEQUENCE: 9

Ile Ile Ile Leu Ile Ile Phe Ile Phe Arg Arg Asp Leu Leu Cys Pro
1               5                   10                  15

Leu Gly Ala Leu
            20

<210> SEQ ID NO 10
<211> LENGTH: 15
<212> TYPE: PRT
<213> ORGANISM: Artificial
<220> FEATURE:
```

-continued

<223> OTHER INFORMATION: An artificially synthesized peptide sequence

<400> SEQUENCE: 10

Ile Phe Ile Phe Arg Arg Asp Leu Leu Cys Pro Leu Gly Ala Leu
1               5                   10                  15

<210> SEQ ID NO 11
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 11

Ile Ile Leu Ile Ile Phe Ile Phe Arg Arg Asp Leu
1               5                   10

<210> SEQ ID NO 12
<211> LENGTH: 13
<212> TYPE: PRT
<213> ORGANISM: Artificial
<220> FEATURE:
<223> OTHER INFORMATION: An artificially synthesized peptide sequence

<400> SEQUENCE: 12

Ile Ile Ile Leu Ile Ile Phe Ile Phe Arg Arg Asp Leu
1               5                   10

<210> SEQ ID NO 13
<211> LENGTH: 12
<212> TYPE: PRT
<213> ORGANISM: Artificial
<220> FEATURE:
<223> OTHER INFORMATION: An artificially synthesized peptide sequence

<400> SEQUENCE: 13

Ile Ile Ile Leu Ile Ile Phe Ile Phe Arg Arg Asp
1               5                   10

<210> SEQ ID NO 14
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 14

Ile Ile Ile Leu Ile Ile Phe Ile Phe Arg Arg
1               5                   10

<210> SEQ ID NO 15
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 15

Ile Ile Ile Leu Ile Ile Phe Ile Phe Arg
1               5                   10

<210> SEQ ID NO 16
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 16

Ile Ile Ile Leu Ile Ile Phe Ile Phe
1               5

<210> SEQ ID NO 17
<211> LENGTH: 8
<212> TYPE: PRT
<213> ORGANISM: Artificial
<220> FEATURE:
<223> OTHER INFORMATION: An artificially synthesized peptide sequence

<400> SEQUENCE: 17

Ile Ile Ile Leu Ile Ile Phe Ile
1               5

<210> SEQ ID NO 18
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 18

Ile Ile Ile Leu Ile Ile Phe
1               5

<210> SEQ ID NO 19
<211> LENGTH: 20
<212> TYPE: PRT
<213> ORGANISM: Artificial
<220> FEATURE:
<223> OTHER INFORMATION: An artificially synthesized peptide sequence

<400> SEQUENCE: 19

Arg Arg Pro Phe Phe His Pro Val Gly Glu Ala Asp Tyr Phe Glu Tyr
1               5                   10                  15

His Gln Glu Gly
            20

<210> SEQ ID NO 20
<211> LENGTH: 20
<212> TYPE: PRT
<213> ORGANISM: Artificial
<220> FEATURE:
<223> OTHER INFORMATION: An artificially synthesized peptide sequence

<400> SEQUENCE: 20

Glu Gly Thr Trp Val Ala Gly Val Phe Val Tyr Gly Gly Ser Lys Thr
1               5                   10                  15

Ser Leu Tyr Asn
            20

<210> SEQ ID NO 21
<211> LENGTH: 20
<212> TYPE: PRT
<213> ORGANISM: Artificial
<220> FEATURE:
<223> OTHER INFORMATION: An artificially synthesized peptide sequence

<400> SEQUENCE: 21

Val Phe Val Tyr Gly Gly Ser Lys Thr Ser Leu Tyr Asn Leu Arg Arg
1               5                   10                  15

Gly Thr Ala Leu
            20
```

-continued

<210> SEQ ID NO 22
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 22

Val Tyr Gly Gly Ser Lys Thr Ser Leu
1               5

<210> SEQ ID NO 23
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 23
aagcttgcca ccatgagtga ctggactgga                                    30

<210> SEQ ID NO 24
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 24
ttgaattctt agtcatagta gcttagctga                                    30

<210> SEQ ID NO 25
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 25

Tyr Leu Leu Glu Met Leu Trp Arg Leu
1               5

<210> SEQ ID NO 26
<211> LENGTH: 21
<212> TYPE: RNA
<213> ORGANISM: Artificial
<220> FEATURE:
<223> OTHER INFORMATION: An artificially synthesized oligonucleotide
      for shRNA

<400> SEQUENCE: 26
aagugaagga ggucagguau a                                             21

<210> SEQ ID NO 27
<211> LENGTH: 21
<212> TYPE: RNA
<213> ORGANISM: Artificial
<220> FEATURE:
<223> OTHER INFORMATION: An artificially synthesized oligonucleotide
      for shRNA

<400> SEQUENCE: 27
agauuaaccc uuaccugcuu u                                             21

<210> SEQ ID NO 28
<211> LENGTH: 37
<212> TYPE: DNA
<213> ORGANISM: Artificial

```
<220> FEATURE:
<223> OTHER INFORMATION: An artificially synthesized primer sequence

<400> SEQUENCE: 28
aagcttgcca ccatgtctga cgaggggcca ggtacag                              37

<210> SEQ ID NO 29
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 29
gaattctcac tcctgccctt cctcaccctc                                      30

<210> SEQ ID NO 30
<211> LENGTH: 11
<212> TYPE: PRT
<213> ORGANISM: Artificial
<220> FEATURE:
<223> OTHER INFORMATION: An artificially synthesized peptide sequence

<400> SEQUENCE: 30

His Pro Val Gly Glu Ala Asp Tyr Phe Glu Tyr
1               5                   10

<210> SEQ ID NO 31
<211> LENGTH: 13
<212> TYPE: PRT
<213> ORGANISM: Artificial
<220> FEATURE:
<223> OTHER INFORMATION: An artificially synthesized peptide sequence

<400> SEQUENCE: 31

Val Phe Val Tyr Gly Gly Ser Lys Thr Ser Leu Tyr Asn
1               5                   10

<210> SEQ ID NO 32
<211> LENGTH: 51
<212> TYPE: DNA
<213> ORGANISM: Artificial
<220> FEATURE:
<223> OTHER INFORMATION: An artificially synthesized primer sequence

<400> SEQUENCE: 32
aaccatgggc agccattcta tgcgctattt ttacaccgct gtgtcccggc c              51

<210> SEQ ID NO 33
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 33
aaggatcctg gctcccatct cagggtgagg                                      30

<210> SEQ ID NO 34
<211> LENGTH: 343
<212> TYPE: PRT
<213> ORGANISM: Epstein-Barr virus

<400> SEQUENCE: 34

Met Ser Asp Trp Thr Gly Gly Ala Leu Leu Val Leu Tyr Ser Phe Ala
1               5                   10                  15
```

```
Leu Met Leu Ile Ile Ile Leu Ile Ile Phe Ile Phe Arg Arg Asp
         20                  25                  30

Leu Leu Cys Pro Leu Gly Ala Leu Cys Ile Leu Leu Met Ile Thr
     35                  40                  45

Leu Leu Leu Ile Ala Leu Trp Asn Leu His Gly Gln Ala Leu Phe Leu
 50                  55                  60

Gly Ile Val Leu Phe Ile Phe Gly Cys Leu Leu Val Leu Gly Ile Trp
 65                  70                  75                  80

Ile Tyr Leu Leu Glu Met Leu Trp Arg Leu Gly Ala Thr Ile Trp Gln
                 85                  90                  95

Leu Leu Ala Phe Phe Leu Ala Phe Phe Leu Asp Leu Ile Leu Leu Ile
             100                 105                 110

Ile Ala Leu Tyr Leu Gln Gln Asn Trp Trp Thr Leu Leu Val Asp Leu
         115                 120                 125

Leu Trp Leu Leu Leu Phe Leu Ala Ile Leu Ile Trp Met Tyr Tyr His
     130                 135                 140

Gly Gln Arg His Ser Asp Glu His His His Asp Ser Leu Pro His
145                 150                 155                 160

Pro Gln Gln Ala Thr Asp Asp Ser Gly His Glu Ser Asp Ser Asn Ser
                 165                 170                 175

Asn Glu Gly Arg His His Leu Leu Val Ser Gly Ala Gly Asp Gly Pro
             180                 185                 190

Pro Leu Cys Ser Gln Asn Leu Gly Ala Pro Gly Gly Pro Asp Asn
         195                 200                 205

Gly Pro Gln Asp Pro Asp Asn Thr Asp Asp Asn Gly Pro Gln Asp Pro
 210                 215                 220

Asp Asn Thr Asp Asp Asn Gly Pro His Asp Pro Leu Pro Gln Asp Pro
225                 230                 235                 240

Asp Asn Thr Asp Asp Asn Gly Pro Gln Asp Pro Asp Asn Thr Asp
                 245                 250                 255

Asn Gly Pro His Asp Pro Leu Pro His Ser Pro Ser Asp Ser Ala Gly
             260                 265                 270

Asn Asp Gly Gly Pro Pro Gln Leu Thr Glu Glu Val Glu Asn Lys Gly
         275                 280                 285

Gly Asp Gln Gly Pro Pro Leu Met Thr Asp Gly Gly Gly His Ser
 290                 295                 300

His Asp Ser Gly His Gly Gly Asp Pro His Leu Pro Thr Leu Leu
305                 310                 315                 320

Leu Gly Ser Ser Gly Ser Gly Gly Asp Asp Asp Pro His Gly Pro
                 325                 330                 335

Val Gln Leu Ser Tyr Tyr Asp
             340

<210> SEQ ID NO 35
<211> LENGTH: 1032
<212> TYPE: DNA
<213> ORGANISM: Epstein-Barr virus

<400> SEQUENCE: 35
atgagtgact ggactggagg agccctcctt gtcctctatt cctttgctct catgcttata      60
attataattt tgatcatctt tatcttcaga agagaccttc tctgtccact ggagcccctt     120
tgtatactcc tactgatgat caccctcctg ctcatcgctc tctggaattt gcacggacag     180
gcattgttcc ttggaattgt gctgttcatc ttcgggtgct tacttgtctt aggtatctgg     240
atctacttat tggagatgct ctggcgactt ggtgccacca tctggcagct tttggccttc     300
```

```
ttcctagcct tcttcctaga cctcatcctg ctcattattg ctctctatct acaacaaaac    360
tggtggactc tattggttga tctccttggg ctcctcctgt ttctggcgat tttaatctgg    420
atgtattacc atggacaacg acacagtgat gaacaccacc acgatgactc cctcccgcac    480
cctcaacaag ctaccgatga ttctggccat gaatctgact ctaactccaa cgagggcaga    540
caccacctgc tcgtgagtgg agccggcgac ggaccccccac tctgctctca aaacctaggc    600
gcacctggag gtggtcctga caatggccca caggaccctg acaacactga tgacaatggc    660
ccacaggacc ctgacaacac tgatgacaat ggcccacatg acccgctgcc tcaggaccct    720
gacaacactg atgacaatgg cccacaggac cctgacaaca ctgatgacaa tggcccacat    780
gacccgctgc tcatagccc  tagcgactct gctggaaatg atggaggccc tccacaattg    840
acggaagagg ttgaaaacaa aggaggtgac cagggcccgc ctttgatgac agacggaggc    900
ggcggtcata gtcatgattc cggccatggc ggcggtgatc cacaccttcc tacgctgctt    960
ttgggttctt ctggttccgg tggagatgat gacgaccccc acggcccagt tcagctaagc   1020
tactatgact aa                                                      1032
```

<210> SEQ ID NO 36
<211> LENGTH: 641
<212> TYPE: PRT
<213> ORGANISM: Epstein-Barr virus

<400> SEQUENCE: 36

```
Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Gly Ala Gly Gly Ala Gly Ala Gly
            100                 105                 110

Gly Gly Ala Gly Ala Gly Gly Ala Gly Gly Ala Gly Ala Gly Gly Gly
        115                 120                 125

Gly Ala Gly Ala Gly Gly Ala Gly Gly Ala Gly Gly Ala Gly Gly Ala
    130                 135                 140

Gly Gly Gly Ala Gly Ala Gly Gly Gly Ala Gly Gly Ala Gly Ala Gly
145                 150                 155                 160

Gly Gly Ala Gly Gly Ala Gly Gly Ala Gly Ala Gly Gly Ala Gly Ala
                165                 170                 175

Ala Gly Gly Gly Ala Gly Gly Ala Gly Ala Gly Gly Ala Gly Ala Gly
            180                 185                 190

Ala Gly Gly Ala Gly Ala Gly Gly Ala Gly Ala Gly Gly Ala Gly Gly
        195                 200                 205

Gly Ala Gly Gly Ala Gly Ala Gly Gly Ala Gly Ala Gly Gly Gly Ala
    210                 215                 220

Gly Gly Ala Gly Gly Ala Gly Ala Gly Gly Ala Gly Ala Gly Gly Ala
225                 230                 235                 240
```

-continued

```
Gly Ala Gly Gly Ala Gly Ala Gly Gly Ala Gly Ala Gly
            245                 250                 255

Gly Ala Gly Gly Ala Gly Ala Gly Gly Ala Gly Ala Gly
            260                 265                 270

Gly Gly Ala Gly Gly Ala Gly Ala Gly Gly Ala Gly Ala Gly
            275                 280                 285

Ala Gly Gly Ala Gly Gly Ala Gly Ala Gly Gly Ala Gly
            290                 295                 300

Ala Gly Gly Ala Gly Gly Ala Gly Gly Ala Gly Ala Gly
305                 310                 315                 320

Gly Ala Gly Ala Gly Gly Gly Arg Gly Arg Gly Ser Gly Gly
                325                 330                 335

Arg Gly Arg Gly Gly Ser Gly Gly Arg Gly Arg Gly Ser Gly Gly
            340                 345                 350

Arg Arg Gly Arg Gly Arg Glu Arg Ala Arg Gly Gly Ser Arg Glu Arg
            355                 360                 365

Ala Arg Gly Arg Gly Arg Gly Arg Gly Glu Lys Arg Pro Arg Ser Pro
370                 375                 380

Ser Ser Gln Ser Ser Ser Ser Gly Ser Pro Pro Arg Arg Pro Pro
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
                420                 425                 430

Ala Ile Glu Gln Gly Pro Ala Asp Asp Pro Gly Glu Gly Pro Ser Thr
            435                 440                 445

Gly Pro Arg Gly Gln Gly Asp Gly Gly Arg Arg Lys Lys Gly Gly Trp
450                 455                 460

Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
                500                 505                 510

Ser Lys Thr Ser Leu Tyr Asn Leu Arg Arg Gly Thr Ala Leu Ala Ile
            515                 520                 525

Pro Gln Cys Arg Leu Thr Pro Leu Ser Arg Leu Pro Phe Gly Met Ala
530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Thr Cys Asn
            580                 585                 590

Ile Arg Val Thr Val Cys Ser Phe Asp Asp Gly Val Asp Leu Pro Pro
            595                 600                 605

Trp Phe Pro Pro Met Val Glu Gly Ala Ala Glu Gly Asp Asp Gly
            610                 615                 620

Asp Asp Gly Asp Glu Gly Gly Asp Gly Asp Glu Gly Glu Glu Gly Gln
625                 630                 635                 640

Glu
```

<210> SEQ ID NO 37
<211> LENGTH: 1926
<212> TYPE: DNA
<213> ORGANISM: Epstein-Barr virus

<400> SEQUENCE: 37

| | | | | | |
|---|---|---|---|---|---|
| atgtctgacg | aggggccagg | tacaggacct | ggaaatggcc | taggagagaa | gggagacaca | 60 |
| tctggaccag | aaggctccgg | cggcagtgga | cctcaaagaa | gaggggtga | taaccatgga | 120 |
| cgaggacggg | gaagaggacg | aggacgagga | ggcggaagac | caggagcccc | gggcggctca | 180 |
| ggatcagggc | caagacatag | agatggtgtc | cggagacccc | aaaaacgtcc | aagttgcatt | 240 |
| ggctgcaaag | ggacccacgg | tggaacagga | gcaggagcag | gagcgggagg | ggcaggagca | 300 |
| ggaggggcag | gagcaggagg | aggggcagga | gcaggaggag | gggcaggagg | ggcaggaggg | 360 |
| gcaggagggg | caggagcagg | aggaggggca | ggagcaggag | gaggggcagg | aggggcagga | 420 |
| ggggcaggag | caggaggagg | ggcaggagca | ggaggagggg | caggaggggc | aggagcagga | 480 |
| ggaggggcag | gaggggcagg | aggggcagga | gcaggaggag | gggcaggagc | aggaggaggg | 540 |
| gcaggagggg | caggagcagg | aggaggggca | ggaggggcag | gaggggcagg | agcaggagga | 600 |
| ggggcaggag | caggaggggc | aggaggggca | ggaggggcag | gagcaggagg | ggcaggagca | 660 |
| ggaggagggg | caggaggggc | aggaggggca | ggagcaggag | gggcaggagc | aggaggggca | 720 |
| ggagcaggag | gggcaggagc | aggaggggca | ggaggggcag | gagcaggagg | ggcaggaggg | 780 |
| gcaggagcag | gaggggcagg | aggggcagga | gcaggaggag | gggcaggagg | ggcaggagca | 840 |
| ggaggagggg | caggaggggc | aggagcagga | ggggcaggag | gggcaggagc | aggagggca | 900 |
| ggaggggcag | gagcaggagg | ggcaggaggg | gcaggagcag | gaggagggc | aggagcagga | 960 |
| ggggcaggag | caggaggtgg | aggccggggt | cgaggaggca | gtggaggccg | gggtcgagga | 1020 |
| ggtagtggag | gccggggtcg | aggaggtagt | ggaggccgcc | ggggtagagg | acgtgaaaga | 1080 |
| gccagggggg | gaagtcgtga | aagagccagg | gggagaggtc | gtggacgtgg | agaaaagagg | 1140 |
| cccaggagtc | ccagtagtca | gtcatcatca | tccgggtctc | caccgcgcag | gcccccctcca | 1200 |
| ggtagaaggc | cattttttcca | ccctgtaggg | gaagccgatt | attttgaata | ccaccaagaa | 1260 |
| ggtggcccag | atggtgagcc | tgacgtgccc | ccgggagcga | tagagcaggg | ccccgcagat | 1320 |
| gacccaggag | aaggcccaag | cactggaccc | cggggtcagg | gtgatggagg | caggcgcaaa | 1380 |
| aaaggagggt | ggtttggaaa | gcatcgtggt | caaggaggtt | ccaacccgaa | atttgagaac | 1440 |
| attgcagaag | gtttaagagc | tctcctggct | aggagtcacg | tagaaaggac | taccgacgaa | 1500 |
| ggaacttggg | tcgccggtgt | gttcgtatat | ggaggtagta | agacctccct | ttacaaccta | 1560 |
| aggcgaggaa | ctgcccttgc | tattccacaa | tgtcgtctta | caccattgag | tcgtctcccc | 1620 |
| tttggaatgg | cccctggacc | cggcccacaa | cctggcccgc | taagggagtc | cattgtctgt | 1680 |
| tatttcatgg | tcttttttaca | aactcatata | tttgctgagg | ttttgaagga | tgcgattaag | 1740 |
| gaccttgtta | tgacaaagcc | cgctcctacc | tgcaatatca | gggtgactgt | gtgcagcttt | 1800 |
| gacgatggag | tagatttgcc | tccctggttt | ccacctatgg | tggaagggc | tgccgcggag | 1860 |
| ggtgatgacg | gagatgacgg | agatgaagga | ggtgatggag | atgagggtga | ggaagggcag | 1920 |
| gagtga | | | | | 1926 |

<210> SEQ ID NO 38
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 38

Arg Lys Lys Arg Arg Gln Arg Arg Arg
1               5
```